(12) United States Patent
Jørgensen et al.

(10) Patent No.: US 9,186,465 B2
(45) Date of Patent: Nov. 17, 2015

(54) ELECTRONICALLY ASSISTED DRUG DELIVERY DEVICE

(75) Inventors: Bjarke Dupont Jørgensen, Jyllinge (DK); Jan Lindhardt Petersen, Søborg (DK); Steven Linnebjerg, Skævinge (DK); Henrik Groth Ludvigsen, Lynge (DK); Michael Ejstrup Hansen, Morud (DK); Erik Beyerholm, Holte (DK); Ramin Nateghi Elahi, Gørløse (DK)

(73) Assignee: Novo Nordisk A/S, Bagsvaerd (DK)

( * ) Notice: Subject to any disclaimer, the term of this patent is extended or adjusted under 35 U.S.C. 154(b) by 1102 days.

(21) Appl. No.: 13/126,378

(22) PCT Filed: Nov. 5, 2009

(86) PCT No.: PCT/EP2009/064692
§ 371 (c)(1),
(2), (4) Date: Jul. 15, 2011

(87) PCT Pub. No.: WO2010/052275
PCT Pub. Date: May 14, 2010

(65) Prior Publication Data
US 2011/0270214 A1 Nov. 3, 2011

Related U.S. Application Data

(60) Provisional application No. 61/111,858, filed on Nov. 6, 2008.

(51) Int. Cl.
*A61M 5/31* (2006.01)
*A61M 5/315* (2006.01)
*A61M 5/24* (2006.01)

(52) U.S. Cl.
CPC ............. *A61M 5/31551* (2013.01); *A61M 5/24* (2013.01); *A61M 5/3157* (2013.01);
(Continued)

(58) Field of Classification Search
CPC ..................... A61M 5/31546; A61M 5/31551; A61M 5/31568; A61M 2005/2488; A61M 2205/3592; A61M 5/31535; A61M 5/31543; A61M 5/31558; A61M 5/3157; A61M 5/31575; A61M 5/3158; A61M 2005/2407; A61M 2005/3125; A61M 2005/3126; A61M 2005/3152; A61M 2205/3553; A61M 2205/3561; A61M 2205/50; A61M 2205/52; A61M 2205/8206
USPC ................................................. 604/207–211
See application file for complete search history.

(56) References Cited

U.S. PATENT DOCUMENTS 3,700,862 A 10/1972 Snook et al.
3,809,863 A 5/1974 Oberg
(Continued)

FOREIGN PATENT DOCUMENTS

JP 62/239019 A 10/1987
JP 08/159704 A 6/1996
(Continued)

*Primary Examiner* — Theodore Stigell
(74) *Attorney, Agent, or Firm* — Wesley Nicolas

(57) ABSTRACT

The present invention relates to electronically assisted drug delivery devices (100). The drug delivery device may include a Gray code type detector for sensing dosage data, wherein the detector comprises a code track consisting of a sequence of alternating markings and a plurality of detectors that are mutually spaced in a direction extending along the code track. The drug delivery device may also include a dosage selector (260) which is moved in a proximal direction upon dose setting and in a distal direction upon dose injection, where the dosage selector is latched in the end of dose position by a latching element, the latching element actuating an end of dose switch for signalling the end of dose state. The drug delivery device may also incorporate power-management arrangements which effectively minimizes power consumption for the incorporated electronic circuitry.

12 Claims, 17 Drawing Sheets

Figure 1:
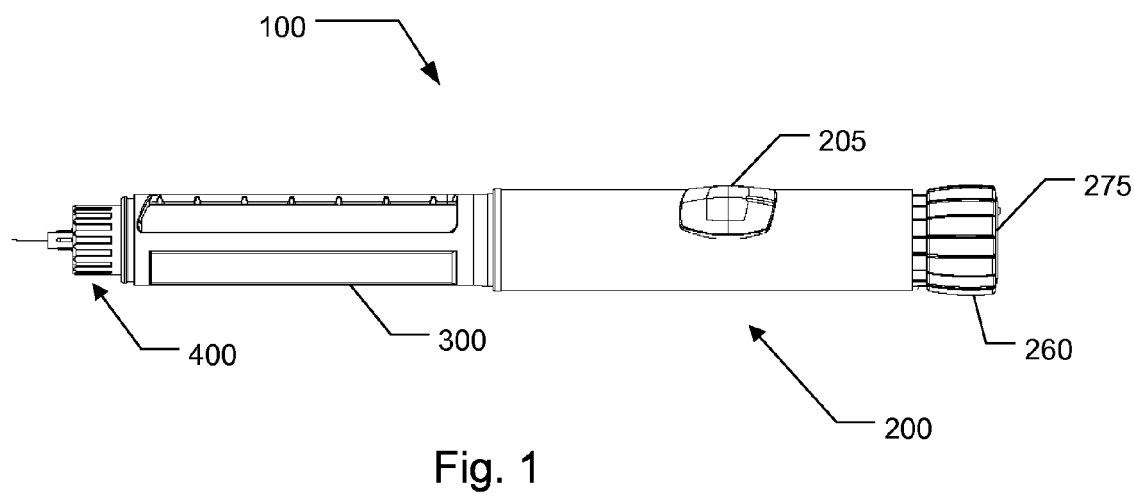

(52) U.S. Cl.
CPC ......... *A61M 5/3158* (2013.01); *A61M 5/31535* (2013.01); *A61M 5/31543* (2013.01); *A61M 5/31558* (2013.01); *A61M 5/31575* (2013.01); *A61M 2005/2407* (2013.01); *A61M 2005/2488* (2013.01); *A61M 2005/3125* (2013.01); *A61M 2005/3126* (2013.01); *A61M 2005/3152* (2013.01); *A61M 2205/3553* (2013.01); *A61M 2205/3561* (2013.01); *A61M 2205/3592* (2013.01); *A61M 2205/50* (2013.01); *A61M 2205/52* (2013.01); *A61M 2205/8206* (2013.01)

(56) References Cited

U.S. PATENT DOCUMENTS

| | | |
|---|---|---|
| 3,916,157 A | 10/1975 | Roulette et al. |
| 3,998,513 A | 12/1976 | Kobayashi et al. |
| 4,179,212 A | 12/1979 | Lahr |
| 4,327,283 A | 4/1982 | Heyman et al. |
| 4,355,300 A | 10/1982 | Weber |
| 4,420,754 A | 12/1983 | Andermo |
| 4,449,042 A | 5/1984 | Hampson et al. |
| 4,476,149 A | 10/1984 | Poppe et al. |
| 4,476,381 A | 10/1984 | Rubin |
| 4,543,526 A | 9/1985 | Burckhardt et al. |
| 4,591,707 A | 5/1986 | Stenzel et al. |
| 4,625,101 A | 11/1986 | Hinks et al. |
| 4,636,786 A | 1/1987 | Haertling |
| 4,693,574 A | 9/1987 | Ohnuki et al. |
| 4,731,526 A | 3/1988 | Knoll et al. |
| 4,739,377 A | 4/1988 | Allen |
| 4,810,867 A | 3/1989 | Speicher |
| 4,850,966 A | 7/1989 | Grau et al. |
| 4,853,521 A | 8/1989 | Claeys et al. |
| 4,857,716 A | 8/1989 | Gombrich et al. |
| 4,880,014 A | 11/1989 | Zarowitz et al. |
| 4,896,946 A | 1/1990 | Suzuki et al. |
| 4,930,263 A | 6/1990 | Rando |
| 4,950,246 A | 8/1990 | Muller |
| 4,959,056 A | 9/1990 | Dombrowski et al. |
| 4,978,335 A | 12/1990 | Arthur, III |
| 5,053,715 A | 10/1991 | Andermo |
| 5,059,776 A | 10/1991 | Antes |
| 5,077,635 A | 12/1991 | Bollhagen et al. |
| 5,078,683 A | 1/1992 | Sancoff et al. |
| 5,091,798 A | 2/1992 | Hibino |
| 5,132,026 A | 7/1992 | Baluyot et al. |
| 5,153,827 A | 10/1992 | Coutre et al. |
| 5,174,766 A | 12/1992 | Yoshizawa et al. |
| 5,176,502 A | 1/1993 | Sanderson et al. |
| 5,196,683 A | 3/1993 | Marom et al. |
| 5,271,527 A | 12/1993 | Haber et al. |
| 5,305,147 A | 4/1994 | Hasegawa et al. |
| 5,311,364 A | 5/1994 | Kanoshima et al. |
| 5,317,506 A | 5/1994 | Coutre et al. |
| 5,336,871 A | 8/1994 | Colgate, Jr. |
| 5,379,131 A | 1/1995 | Yamazaki |
| 5,394,206 A | 2/1995 | Cocca |
| 5,403,616 A | 4/1995 | Hattori et al. |
| 5,418,649 A | 5/1995 | Igarashi |
| 5,422,472 A | 6/1995 | Tavislan et al. |
| 5,430,278 A | 7/1995 | Krieg et al. |
| 5,432,329 A | 7/1995 | Colgate, Jr. et al. |
| 5,461,239 A | 10/1995 | Atherton |
| 5,523,560 A | 6/1996 | Manique et al. |
| 5,569,212 A | 10/1996 | Brown |
| 5,585,615 A | 12/1996 | Iwanami et al. |
| 5,593,390 A | 1/1997 | Castellano et al. |
| 5,628,309 A | 5/1997 | Brown |
| 5,637,854 A | 6/1997 | Thomas |
| 5,643,212 A | 7/1997 | Coutre et al. |
| 5,675,380 A | 10/1997 | Florent et al. |
| 5,686,725 A | 11/1997 | Maruyama et al. |
| 5,747,350 A | 5/1998 | Sattler |
| 5,757,521 A | 5/1998 | Walters et al. |
| 5,764,457 A | 6/1998 | Uhde et al. |
| 5,777,303 A | 7/1998 | Berney |
| 5,782,814 A | 7/1998 | Brown et al. |
| 5,786,584 A | 7/1998 | Button et al. |
| 5,791,880 A | 8/1998 | Wilson |
| 5,792,117 A | 8/1998 | Brown |
| 5,793,502 A | 8/1998 | Bianco et al. |
| 5,821,521 A | 10/1998 | Bridgelall et al. |
| 5,821,524 A | 10/1998 | Horlbeck et al. |
| 5,876,380 A | 3/1999 | Manganini et al. |
| 5,880,683 A | 3/1999 | Brandestini |
| 5,882,463 A | 3/1999 | Tompkin et al. |
| 5,886,519 A | 3/1999 | Masreliez et al. |
| 5,895,369 A | 4/1999 | Flower |
| 5,902,990 A | 5/1999 | Stewart |
| 5,920,198 A | 7/1999 | Suzuki et al. |
| 5,925,867 A | 7/1999 | Hagimoto |
| 5,928,201 A | 7/1999 | Poulsen et al. |
| 5,954,700 A | 9/1999 | Kovelman |
| 5,986,585 A | 11/1999 | Pusch |
| 6,003,775 A | 12/1999 | Ackley |
| 6,019,745 A | 2/2000 | Gray |
| 6,047,892 A | 4/2000 | Schuessler et al. |
| 6,053,415 A | 4/2000 | Norwood |
| 6,068,615 A | 5/2000 | Brown et al. |
| 6,090,064 A | 7/2000 | Reilly et al. |
| 6,110,148 A | 8/2000 | Brown et al. |
| 6,110,152 A | 8/2000 | Kovelman |
| 6,168,080 B1 | 1/2001 | Verschuur et al. |
| 6,177,683 B1 | 1/2001 | Kolesar et al. |
| 6,202,929 B1 | 3/2001 | Verschuur et al. |
| 6,215,508 B1 | 4/2001 | Bryan et al. |
| 6,265,466 B1 | 7/2001 | Glatkowski et al. |
| 6,274,092 B1 | 8/2001 | Itoh |
| 6,329,813 B1 | 12/2001 | Andermo |
| 6,352,523 B1 | 3/2002 | Brown et al. |
| 6,372,293 B1 | 4/2002 | Mathus et al. |
| 6,435,175 B1 | 8/2002 | Stenzler |
| 6,475,192 B1 | 11/2002 | Reilly et al. |
| 6,533,183 B2 | 3/2003 | Aasmul et al. |
| 6,598,796 B2 | 7/2003 | Harrop |
| 6,652,812 B1 | 11/2003 | Vartiainen et al. |
| 6,669,090 B2 | 12/2003 | Eilersen |
| 6,700,391 B2 | 3/2004 | Strack et al. |
| 6,813,868 B2 | 11/2004 | Baldwin et al. |
| 6,854,653 B2 | 2/2005 | Eilersen |
| 6,876,209 B2 | 4/2005 | Lin et al. |
| 6,954,700 B2 | 10/2005 | Higashida et al. |
| 6,957,522 B2 | 10/2005 | Baldwin et al. |
| 6,976,349 B2 | 12/2005 | Baldwin et al. |
| 6,994,261 B2 | 2/2006 | Eilersen |
| 7,018,363 B2 | 3/2006 | Cowan et al. |
| 7,041,941 B2 | 5/2006 | Faries, Jr. et al. |
| 7,061,831 B2 | 6/2006 | De La Huerga |
| 7,077,332 B2 | 7/2006 | Verschuur et al. |
| 7,104,973 B2 | 9/2006 | Woolston et al. |
| 7,108,184 B2 | 9/2006 | Mase et al. |
| 7,138,806 B2 | 11/2006 | Gafner et al. |
| 7,426,408 B2 | 9/2008 | DeNuzzio et al. |
| 7,521,921 B2 | 4/2009 | Zhu et al. |
| 7,614,545 B2 | 11/2009 | Christoffersen et al. |
| 7,621,456 B2 | 11/2009 | Eilersen |
| 8,049,519 B2 | 11/2011 | Nielsen et al. |
| 8,197,449 B2 | 6/2012 | Nielsen et al. |
| 8,348,904 B2 | 1/2013 | Petersen |
| 2001/0001472 A1 | 5/2001 | Sano et al. |
| 2001/0013544 A1 | 8/2001 | Rathus et al. |
| 2001/0015202 A1 | 8/2001 | Miller |
| 2001/0034506 A1 | 10/2001 | Hirschman et al. |
| 2002/0000471 A1 | 1/2002 | Aasmul et al. |
| 2002/0012176 A1 | 1/2002 | Ning |
| 2002/0020654 A1 | 2/2002 | Eilersen |
| 2002/0022821 A1 | 2/2002 | Eilersen |
| 2002/0063156 A1 | 5/2002 | Marchand |
| 2002/0106309 A1 | 8/2002 | Mathus et al. |
| 2002/0117549 A1 | 8/2002 | Lee |
| 2002/0117579 A1 | 8/2002 | Kotoulas et al. |
| 2002/0123078 A1 | 9/2002 | Seul et al. |
| 2003/0015590 A1 | 1/2003 | Chen |

(56) References Cited

U.S. PATENT DOCUMENTS

| | | |
|---|---|---|
| 2003/0039590 A1 | 2/2003 | Lodge |
| 2003/0116630 A1 | 6/2003 | Carey et al. |
| 2003/0143614 A1 | 7/2003 | Drmanac |
| 2003/0205625 A1 | 11/2003 | Eilersen |
| 2003/0233069 A1 | 12/2003 | Gillespie et al. |
| 2004/0008853 A1 | 1/2004 | Pelrine et al. |
| 2004/0024368 A1 | 2/2004 | Broselow |
| 2004/0046032 A1 | 3/2004 | Urano et al. |
| 2004/0051368 A1 | 3/2004 | Caputo et al. |
| 2004/0141426 A1 | 7/2004 | Kawasaki et al. |
| 2004/0155113 A1 | 8/2004 | Urano et al. |
| 2004/0178255 A1 | 9/2004 | Eich et al. |
| 2004/0200558 A1 | 10/2004 | Stevens et al. |
| 2004/0207385 A1 | 10/2004 | Gafner et al. |
| 2004/0210199 A1* | 10/2004 | Atterbury et al. ............ 604/224 |
| 2004/0243130 A1 | 12/2004 | Biscup |
| 2005/0006472 A1 | 1/2005 | Verschuur et al. |
| 2005/0035207 A1 | 2/2005 | Philyaw et al. |
| 2005/0060059 A1 | 3/2005 | Klein et al. |
| 2005/0116033 A1 | 6/2005 | Moore |
| 2005/0156318 A1 | 7/2005 | Douglas |
| 2005/0182360 A1 | 8/2005 | Yeandel et al. |
| 2005/0236603 A1 | 10/2005 | Faris |
| 2005/0283116 A1 | 12/2005 | Eakins et al. |
| 2006/0097877 A1 | 5/2006 | Baba et al. |
| 2006/0118612 A1 | 6/2006 | Christoffersen et al. |
| 2006/0125491 A1 | 6/2006 | Grishin et al. |
| 2006/0129104 A1 | 6/2006 | Cowan et al. |
| 2006/0138233 A1 | 6/2006 | Kemppainen et al. |
| 2006/0164002 A1 | 7/2006 | O'Brien et al. |
| 2006/0170981 A1 | 8/2006 | Ricks et al. |
| 2006/0175427 A1 | 8/2006 | Jonientz et al. |
| 2006/0176267 A1 | 8/2006 | Honeyman et al. |
| 2006/0224123 A1 | 10/2006 | Friedli et al. |
| 2006/0226238 A1 | 10/2006 | Salib et al. |
| 2006/0243804 A1 | 11/2006 | Christoffersen et al. |
| 2007/0080234 A1 | 4/2007 | Domoy |
| 2007/0239116 A1 | 10/2007 | Follman et al. |
| 2008/0015510 A1 | 1/2008 | Sandoz et al. |
| 2009/0088701 A1 | 4/2009 | Larsen |

FOREIGN PATENT DOCUMENTS

| | | |
|---|---|---|
| JP | 2004-535590 A | 11/2004 |
| WO | 94/15120 | 7/1994 |
| WO | 0195959 | 12/2001 |
| WO | 02/092153 A2 | 11/2002 |
| WO | 02092153 | 11/2002 |
| WO | 03103753 A1 | 12/2003 |
| WO | 2005/110387 | 11/2005 |
| WO | 2005/110387 A2 | 11/2005 |
| WO | 2006/113521 | 10/2006 |
| WO | 2006/113521 A2 | 10/2006 |
| WO | 2006/120182 | 11/2006 |
| WO | 2006/120182 A1 | 11/2006 |
| WO | WO2006/120182 * | 11/2006 |

* cited by examiner

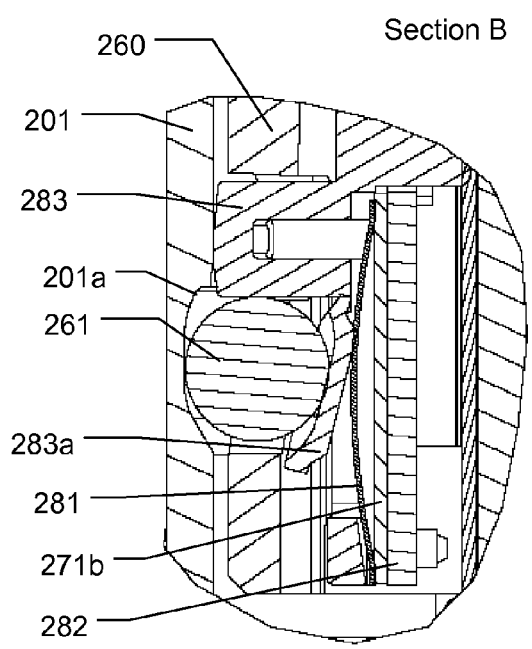
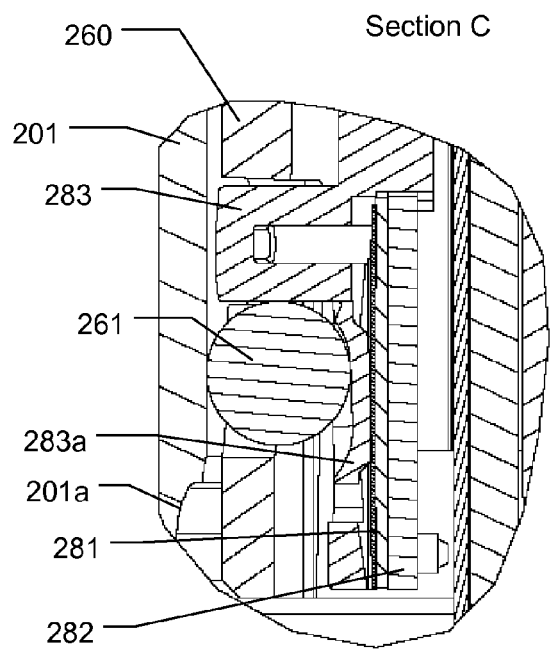
Fig. 12a                Fig. 12b
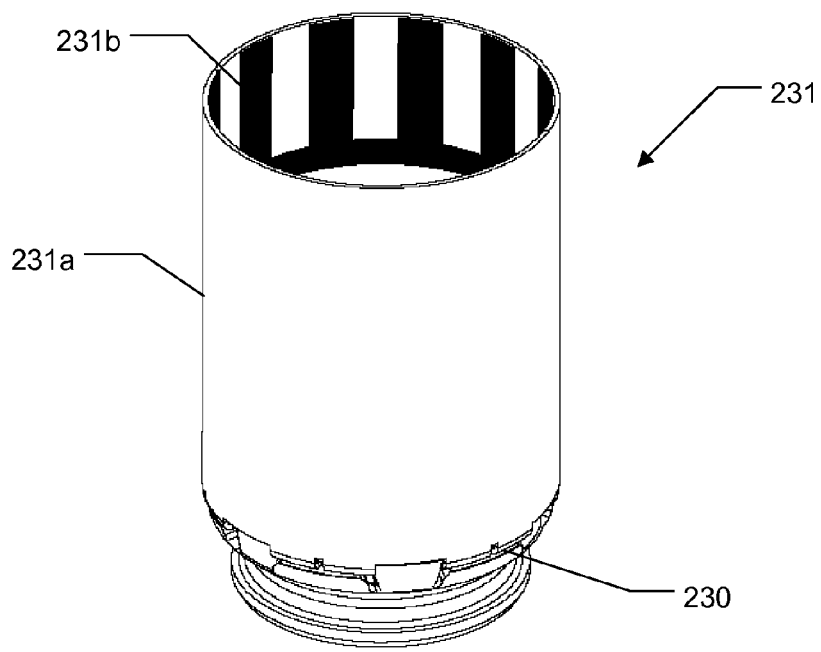
Fig. 13

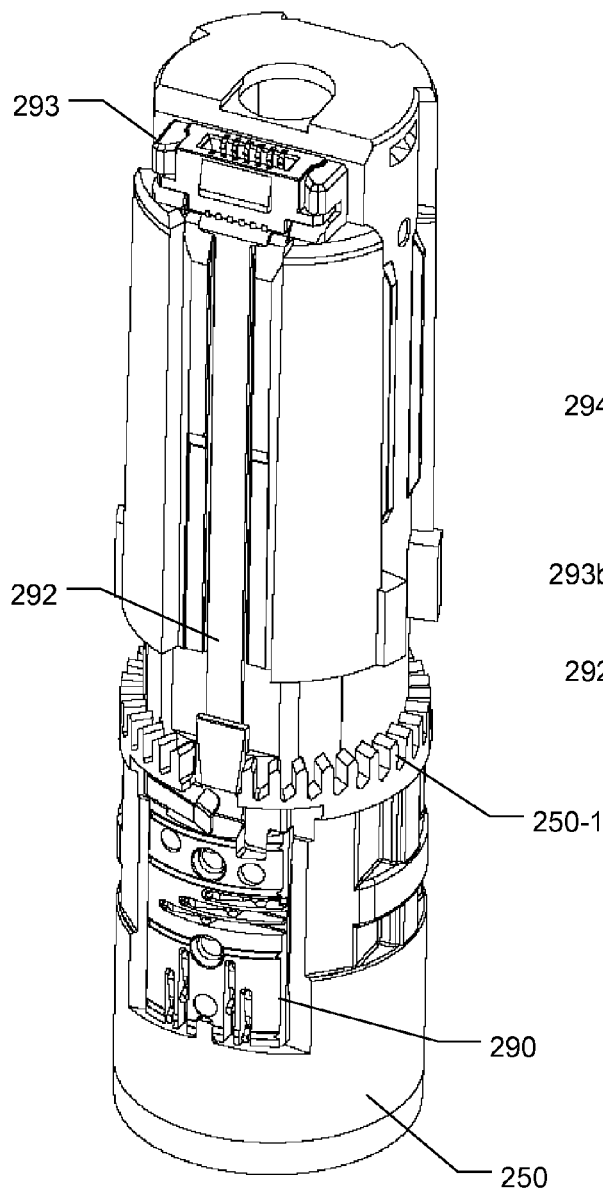
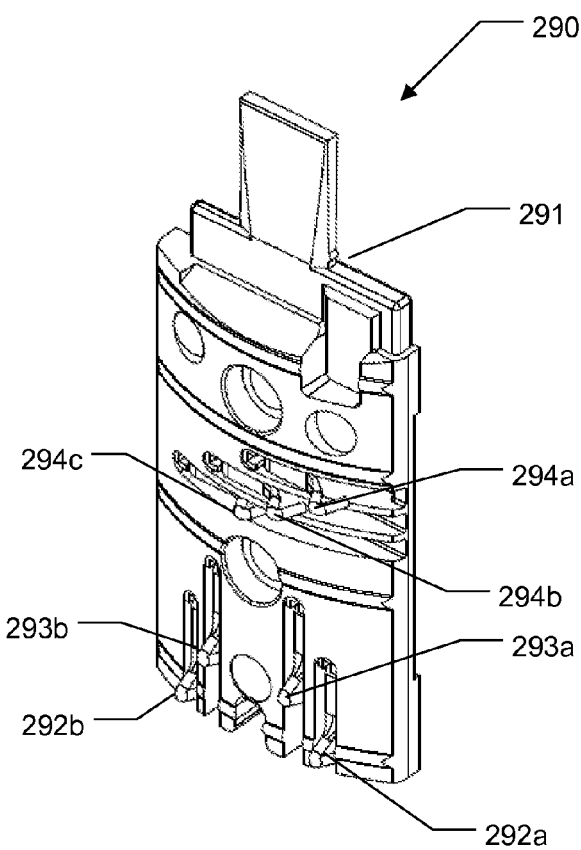
Fig. 14
Fig. 15

| | Switch 4 | Switch 3 | Switch 2 | Switch 1 |
|---|---|---|---|---|
| 0 | 0 | 0 | 1 | 1 |
| 1 | 1 | 0 | 1 | 1 |
| 2 | 1 | 0 | 0 | 1 |
| 3 | 1 | 1 | 0 | 1 |
| 4 | 1 | 1 | 0 | 0 |
| 5 | 1 | 1 | 1 | 0 |
| 6 | 0 | 1 | 1 | 0 |
| 7 | 0 | 1 | 1 | 1 |

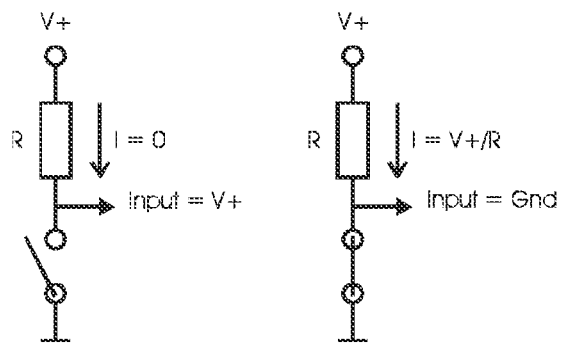 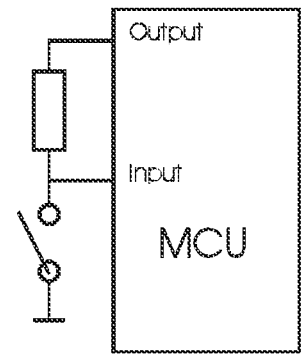
Fig. 20a    Fig. 20b
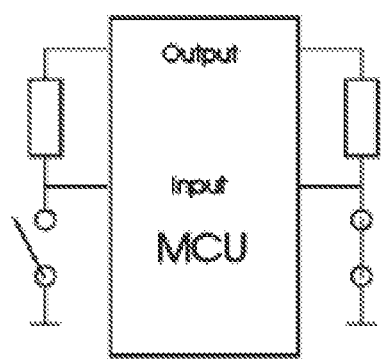
Fig. 20c
| Dosage selector state | End of Dose | Dosage sense |
|---|---|---|
| Pulled out (Dosage setting) | 0 | 1 |
| Depressed (Dosing) | 0 | 0 |
| Locked (EOD) | 1 | 0 |
Fig. 21

ELECTRONICALLY ASSISTED DRUG DELIVERY DEVICE

CROSS-REFERENCE TO RELATED APPLICATIONS

This application is a 35 U.S.C. §371 national stage application of International Patent Application PCT/EP2009/064692 (published as WO2010/052275), filed Nov. 5, 2009, which claims priority under 35 U.S.C. §119 of U.S. Provisional Application 61/111,858, filed Nov. 6, 2008.

FIELD OF THE INVENTION

The present invention relates to electronically assisted drug delivery devices. In particular the present invention relates to measures related to detecting and storing the size of expelled doses from drug delivery devices.

BACKGROUND OF THE INVENTION

Medical drug delivery devices are used to deliver selected doses of medication to patients. Some medication, such as insulin is self-administered. The typical diabetes patient will require injections of insulin several times during the course of the day.

State of the art drug delivery devices, such as the injection device disclosed in WO 01/95959, provides a user friendly and accurate device wherein most demands as regards patient needs are met. However, purely mechanical working injection devices do not provide the possibility of storing information related to previously injected doses for later retrieval.

Some prior art devices, such as the injection device shown in WO 02/92153, include an electronic dose size identifier and an electronic display which can be used to display the size of a currently set dose as well as the dose size of previously injected doses.

In order to provide more user friendly devices the dosage selector of the injection device should preferably include a rotatable dosage selector which can be dialled in very fine increments. In particular in injection devices for delivery of half-incremental units of a medication, the incremental steps when rotating from one dose size to the next consecutive dose size should preferably be very small. This is of particular importance when dialling larger doses which otherwise usually results in the need of rotating the dosage selector several full revolutions. Such "endless" turning typically will be considered as incurring an unnecessary discomfort. The trend of minimizing incremental dose setting steps in drug delivery devices introduce an increase in the demands regarding the accuracy of the detection system for detecting dose sizes.

Another problem with prior art drug delivery devices, is that monitoring of the end of dose condition, i.e. the specific state where a dosing action is fulfilled, may be somewhat imprecise or unreliable, having consequences for the correct monitoring of dose information.

Another problem when designing different versions of an injection device so as to provide different dose increments for different versions, e.g. full incremental devices and half-incremental devices, is that normally, a large number of components have to be redesigned in order for both versions to perform adequately.

Having regard to the above-identified prior art devices, it is an object of the present invention to provide a drug delivery device which enables improved electronic detection of movements in an injection device.

A further object of the invention is to provide an electronic drug delivery device, which optionally can be equipped with means for transferring data with an external device, where the drug delivery device incorporates a power-management which is effective in minimizing power consumption for the incorporated electronic circuitry, yet allows ease of use during operation of the device.

Yet a further object of the invention is to provide measures for obtaining devices having a superior performance and, at the same time, being manufactured at a reduced cost.

BRIEF DESCRIPTION OF THE INVENTION

In a first aspect, the present invention relates to a drug delivery device for delivery of a medicament drug from a held drug reservoir, the device comprising: a) a piston rod adapted to move a piston of the cartridge towards a distal end of the drug delivery device, b) a drive sleeve for driving the piston rod upon exertion of a plunging force, c) a rotatable dose sleeve member for setting a volume of a dose to be expelled from the cartridge, d) a clutch mechanism for coupling and uncoupling the drive sleeve from the dose sleeve member, and e) a rotational position encoder adapted to detect the size of a set dose and/or an expelled dose, the rotational position encoder being operationally coupled to sense data associated with the relative rotational position between two components that rotates relative to each other during dose setting and which does not rotate relatively to each other during dose expelling.

In the device, the clutch mechanism is configured for a state change of the clutch (i.e. coupling or uncoupling) upon exertion of an initial plunging force during expelling and the rotational position encoder is adapted to perform a control reading after said state change of the clutch. The determination of the volume of an expelled dose incorporates data obtained by said control reading. The determination of the volume of an expelled dose may further be based upon data obtained at the end of a previous expelling procedure, at the start of the dose setting procedure and/or during the dose setting procedure so as to provide a starting point to compare with the control reading.

According to the first aspect of the invention, by incorporating a rotational position encoder that is configured to detect relative rotational position changes that exclusively occur during dose setting it is ensured that the position encoder do not impose an increase as regards the necessary dose force for carrying out the expelling of a dose.

In a first embodiment of the first aspect, the drug delivery device includes a clutch mechanism that couples the dose sleeve member and the drive sleeve during dose setting so that the dose sleeve member and the drive sleeve rotates together and wherein the clutch mechanism decouples the dose sleeve member from the drive sleeve during dose expelling so as to allow rotation of the dose sleeve member while preventing rotation of the drive sleeve during dose expelling. In such a configuration, the rotation of the drive sleeve may be monitored during dose setting. When a plunging force is exerted to expel the set dose, the drive sleeve will be locked rotationally relative to the housing and a control reading of the rotational position of the drive sleeve will be carried out after this lock has been effectuated. The said control reading may be performed shortly after the said lock has been established or alternatively at the end of dose expelling, i.e. at the End-Of-Dose state.

In a second embodiment of the first aspect, the drug delivery device includes a clutch mechanism that is so configured that it decouples the dose sleeve member and the drive sleeve during dose setting so that the dose sleeve member rotates during dose setting but the drive sleeve is held rotationally stationary during dose setting. In such embodiment, the clutch mechanism couples the dose sleeve member rotationally to the drive sleeve during dose expelling. In such a configuration, the relative rotation between the dose sleeve member and the drive sleeve is monitored during dose setting. When a plunging force is exerted to expel a dose, the drive sleeve will be locked rotationally relative to the dose sleeve member and a control reading of the relative rotational position of the drive sleeve with respect to the dose sleeve member will be carried out after this lock has been effectuated. The said control reading may be performed shortly after the said lock has been established or alternatively at the end of dose expelling, i.e. at the End-Of-Dose state. For further specification to a drug delivery device incorporating such mechanism, reference is made to WO 99/38554 which discloses a drug delivery device having a dose sleeve member referred to as a "dose scale drum" and a drive sleeve referred to as a "driver tube".

In both the first and second embodiment according to the first aspect, the expelled dose is calculated on the basis of the relative rotational movements during dose setting and taking into account the final rotational position after a rotational lock has been established. Hence, a precise measurement is accomplished which accords for a correct electronical dose reading of a dose expelled from the device.

The drug delivery device according to the first aspect may include a mechanical dose dial scale which is associated with the dose sleeve member either by being integral with the dose sleeve member or as a component which rotates in unison with the dose sleeve member. By incorporating both a mechanical dose dial scale as well as means for electronically detecting the size of an expelled dose and/or a set dose, it is ensured that the basic mechanical features of the device may be used no matter if a fault pertaining to the electronic components should occur. By using the above dose sensing method, it is ensured that the detected expelled values exactly corresponds to the set dose as shown on the mechanical scale, even for precision devices having a large number of distinct dose setting positions pr. revolution.

The dose information obtained by the above sensing scheme may be displayed on an electronic display provided on the drug delivery device or alternatively, or in addition, be transferred to an external device for displaying, for storage or for transmission to a remote server.

The drug delivery device may further include a mechanism which provides a mechanical advantage (i.e. a gearing) between a dosage actuator, e.g. a button to which said plunging force is applied for expelling a dose, and said driver, so that the button is moved a different distance than the piston rod during dose expelling.

According to a further aspect of the invention, a drug delivery device is provided which incorporates a Gray code type detector for detecting relative movements between a first element and a second element during dose setting and/or during injection wherein the Gray code type detector comprises a code track disposed on the first element, the code track consisting of a sequence of markings alternating between two states, and wherein the code track is associated with a plurality of detectors disposed on the second element, each detector being adapted to sense the two states and wherein the plurality of detectors are mutually offset in a direction extending along the code track to provide a reading sequence of a Gray code scheme when the plurality of detectors are moved along the code track.

In accordance with such position encoder, in order to save physical space, a Gray code is created where all detectors use the same contact pattern, only shifted a number of fractional or complete Gray code states along the Gray code track. This way, all detectors can be mounted on the same track, thus reducing the total dimension of the position encoder. Also, such sensor is less vulnerable to tolerances in the direction transverse to the direction along the track.

The Gray code type detector may include alternating first and second areas of respective first and second states, each of the first areas having an extension along the code track of extension $X_1$ and each of the second areas having an extension along the code track of length $X_2$. In some embodiments, the length $X_1$ corresponds to x2. In other embodiments, the length $X_1$ is different from $X_2$. In embodiments wherein the gray type detector is adapted to measure linear movements, said extensions $X_1$ and $X_2$ designates length. In embodiments wherein the gray type detector is adapted to measure rotational movements, the said extensions $X_1$ and $X_2$ designate annular width.

In some embodiments, the code track may be arranged as a circumferential band on a cylindrical surface, either on an interior cylindrical surface or an external cylindrical surface. Said band may comprise a single or a multitude of repeated Gray code sequences and may form a continuous band arranged in a loop. In other embodiments, the Gray code sequence is arranged as a helically extending track. In still other embodiments the Gray code detector is a planar sensor for detecting linear movements.

In some embodiments, the Gray code type detector includes at least one additional area which is sensed by one or more additional detectors, said additional detector(s) being arranged for sensing relative movement between said additional detector(s) and the Gray code track in a direction transverse to the direction along the Gray code sequence. When a drug delivery device includes a dose setting member, the rotational movements of which is detected by the Gray code sensor, the additional detector(s) may be used to detect whether an injection force is applied to an injection button of the drug delivery device.

In some embodiment, the plurality of detectors is at least three, such as four, such as five, such as six or such as seven. In one embodiment, the code track is provided as a conductive material code track having alternating electrical conducting and electrical insulating areas to be sensed by sensors detecting an electrical voltage applied on the electrical conducting code track. In other embodiments, the Gray code type detector is based on optical measurements. In still other embodiments, the Gray code type detector is based on inductive or capacitive sensors.

According to a further aspect of the invention, a drug delivery device is provided which incorporates a reading assembly for detecting relative rotational position changes between a first element and a second element during dose setting and/or during dose injection, wherein the reading assembly is associated with the first element and arranged internally inside a circumferentially arranged code track associated with the second element. As the circumferential code track encircles the reading assembly, a large measuring diameter can be provided enabling improvements in reading accuracy.

According to a further aspect of the invention, a method of providing a set of two different drug delivery devices is provided, the two devices incorporating dose setting mechanism having mutually different dose increments, the method comprising using the same type rotational position encoder, said position encoder having a resolution which is a multiple of both the dose increment for the first device and a multiple of the dose increment for the second device. Said method may further incorporate the step of modifying an algorithm for determining dose volumes based on the signals received from the rotational position encoder.

According to a further aspect of the invention, a drug delivery device for delivery of a medicament drug from a drug reservoir, comprising a dosage selector which is raised in a proximal direction to set a dose and pushed in a distal position to expel the set dose from the drug delivery device, a latch mechanism for latching the dosage selector in the most distal position at the end of dose position, said latch mechanism including one or more latch elements which at least partly moves in a radial direction when said dosage selector is in the end of dose position, the latching of the dosage selector being released upon user manipulation by pulling the dosage selector in the proximal direction, wherein said one or more latch element(s) actuates one or more of said end of dose switch(es) to signal the end of dose position of the dosage selector.

By the described configuration, it is ensured that the detection of the end of dose state is perfectly synchronised with the latching of the end of dose position of the dosage selector, i.e. in a parked position.

At least one of said one or more latch elements are biased towards its latched position either by being forced by a spring element or the latch element itself incorporating a biasing means.

The latch elements may be provided as a ball which is incorporated in a ball lock mechanism configuration for the respective latch element.

In other embodiments, the latch element may be provided as an annular extending spring which is biased radially so as to expand or reduce its diameter upon latching the dosage selector in its latched position.

In some embodiments the drug delivery device includes at least two ends of dose switches which are positioned so as to oppose each other. A first one of said at least two dose switches is activated by a movement of its corresponding latch element in a first direction and a second of said at least two end of dose switches is activated by a movement by its corresponding latch element in a direction substantially opposing said first direction. In such configuration, the said switches form a redundant set of switches for signalling the end of dose position of the dosage selector.

Said switches may be arranged at least 60 degrees apart, such as at least 90 degrees apart, such as at least 120 degrees apart, such as 180 degrees apart.

According to a further aspect of the invention, a drug delivery device for delivery of a drug from a drug reservoir comprises a dosage actuator which is raised in a proximal direction and pushed in a distal direction to expel the set dose from the drug delivery device, an end of dose switch arrangement to signal the end of dose position of the dosage actuator upon completion of expelling of a full dose, wherein the end of dose switch arrangement comprise at least two end of dose switches in a balanced configuration, and wherein said switches forms a redundant set of switches for signalling the end of dose position of the dosage actuator.

The drug delivery device may include a mechanism that transfers the movement of the dosage actuator into a respective movement of a number of switch activation elements which each are dedicated the activation of a respective end of dose switch, where the respective switch activation elements are configured to perform switch movement directions that are mutually differing.

The end of dose switches may be distributed at different angular positions around a main axis, the main axis being defined by the movement of the dosage actuator. In one embodiment, the device includes two ends of dose (EOD) switches which are arranged to oppose each other, such as being separated 90-180 degrees apart. Other embodiments may contain two switches which are arranged less than 90 degrees apart. Still other embodiments may comprise more than two switches, such as three switches arranged approximately 120 degrees apart.

By incorporating the described end of dose configurations into a medical delivery device, a correct end of dose state can be detected where the configuration provides a particularly fail-safe detection both with respect to tolerances and with respect to mechanical stresses which may be applied when the dosage actuator is operated.

According to a still further aspect of the invention, a drug delivery device comprises: a) a switch circuit comprising a controller for monitoring a condition of at least one component of the drug delivery device, the controller having a plurality of input terminals and output terminals, b) a plurality of switches being operated upon a change in condition of said at least one component, each respective switch at a first end connected to a ground voltage level terminal of the controller and at a second end connected to a respective input terminal of the controller, and c) a plurality of pull-up resistors, each pull-up resistor being connected in series with a respective one of said plurality of switches by connecting a first end of the resistor to the respective input terminal and the second end of the resistor to a respective output terminal of the controller. The voltage level of each respective output terminal is controllable from a first voltage level, where a closing of the respective switch is detectable by the respective input terminal, to a second voltage level upon the closing of said switch to operate the respective pull-up resistor at a substantially zero-current state, and further to said first voltage level in response to at least one other of said plurality of switches being closed.

By incorporating a switch circuitry as the one described into the device, it is ensured that the switch detection circuit will only consume power during the time it takes for the switch circuit to transfer from one stable state to another. This is particularly useful in drug delivery devices being powered by an internal electric cell such as a battery. For example, it ensures a long battery life, ultimately enabling use of one and the same battery during the entire lifetime of the device.

In one embodiment, the plurality of switches comprises a first switch and a second switch where the polarity of the first switch is opposite to the polarity of said second switch so as to provide a complementary switch action.

In further embodiments, the plurality of switches comprises first and second switches where the first switch closes upon a component of the device moves from a first position to a second position and where the second switch closes upon said component moves from the second position to a third position. An exemplary embodiment includes said first switch as a switch sensor which senses an end of dose situation and said second switch as a switch sensor which senses whether a pushing force is exerted on a dosage actuator.

Also, in some embodiments, the drug delivery device comprises a dose setting mechanism operable to select a dose of medicine to be delivered from a held reservoir, the drug delivery device further comprising a position encoder for monitoring dose related information by detecting the position of a member which moves during dose setting and/or dose expelling, said position encoder including one or more electrically conductive coded track(s), each track including conductive and non-conductive areas. The said position encoder further comprises an encoding switch circuitry including a plurality of said switches adapted to read said one or more conductive coded tracks as the switches and the electrically conductive coded track(s) move relatively to each other.

By using the above switch circuitry for the encoding switch circuitry, a particularly energy efficient detection configuration is provided, which powers down the pull-up resistors after a detected position change, possibly by the lapse of a given time duration after detecting the position change.

In some embodiments, the one or more electrically conductive coded track(s) forms a single gray code sequence or a multitude of repeated gray code sequences forming a total sequence code length n wherein the plurality of switches of said encoding switch circuitry reading said conductive coded track(s) are three, such as four such as five such as six switches such as seven switches.

The gray code of the position encoder may be so configured that at least one switch of said encoding switch circuitry is closed upon at least every second state change in either direction from a present position, said present position being selected from any of each possible n positions.

In one form, the position encoder includes a single electrically conductive coded track having consecutive conductive and non-conductive areas and where the switches of said encoding switch circuitry is distributed along the single track so as to obtain said single or multitude of repeated gray code sequences.

In other forms, the position encoder includes a plurality of electrically conductive coded tracks forming a matrix including a plurality of columns and rows and where a single or a plurality of switches of said encoding switch circuitry is aligned with a different row of said matrix.

The drug delivery device may includes a rotatable dosage selector being rotatable in a number distinct rotational positions P spanning a single revolution, and wherein the position encoder is adapted to detect the rotational position of the dosage selector, said total sequence code length n being selected as two, three or four times P, meaning that the dosage selector is adapted to be rotated a plurality of full rotations during dose setting.

According to a still further aspect of the invention, a drug delivery device comprises a controller for monitoring a condition of at least one component of the drug delivery device, and a plurality of switches which are operated upon a change in a condition of said at least one component, each switch connected in series to a respective pull-up resistor. The respective switches and pull-up resistors are coupled to the controller, where the controller is adapted to detect the state of the respective switches by monitoring the voltage drop over corresponding ones of said pull-up resistors. The controller is further configured to selectively apply a first voltage level to each respective pull-up resistor for detecting the closing of its respective switch and upon the detection of the closure of said switch, to apply a second voltage level to the corresponding pull-up resistor so as to bring it into a non current conducting state, and to apply the first voltage level to said corresponding pull-up resistor in response to at least one other of said plurality of switches being closed.

Corresponding to a still further aspect of the invention, a drug delivery device is provided, comprising first user-operatable means for setting a dose of drug to be expelled and second user-operatable means for expelling a set dose from a drug reservoir. The device further comprises electronic circuitry for storing and communicating data, the electronic circuitry having a hibernating state and a first operating state, and contact means for energizing the electronic circuitry from the hibernating to the operating state, wherein user manipulation of the first or second user-operatable means actuates the contact means to thereby energize the electronic circuitry from the hibernating to the first operating state.

The first user-operatable means may be in the form of a rotatable member, and the second user-operatable means may be in the form of an axially displaceable member. As an example, a combined user-operatable member being both rotationally and axially displaceable may be implemented to provide the first respectively the second user-operatable means. The drug delivery device may be provided with a mechanical dose setting and expelling means operatable by the first respectively second user-operatable means, just as it may comprise a drug-filled reservoir or being adapted to receive a drug-filled reservoir. In case the drug delivery device is of the motor doser type the first or second user-operatable means could be push buttons on a keyboard.

The electronic circuitry may comprise communication means for wirelessly transmitting and/or receiving data, the communication means having a sleep state in the hibernating state and an energized state in the first operating state. The state for the communication means may be changed from the energized to the sleep state when a first pre-set condition is met, e.g. when (i) the communication means have unsuccessfully tried to establish wireless communication with a corresponding device for a predefined amount of time, (ii) the communication means have unsuccessfully tried to transmit an amount of data to a corresponding device for a predefined amount of time, (iii) the communication means have successfully transmitted an amount of data to a corresponding device, (iv) the first or second user-operatable means are actuated to set a dose respectively to expel a set dose, or the first or second user-operatable means are arranged in a parked position.

In an exemplary embodiment the electronic circuitry has a second operating state, wherein the first operating state has a first level of power consumption and the second operating state has a second lower level of power consumption, wherein the operating state changes from the first to the second level when a first pre-set condition is met, and wherein the operating state changes from the second level to the hibernating state when a second pre-set condition is met.

The electronic circuitry may comprise communication means for wirelessly transmitting and/or receiving data, the communication means having a sleep state in the hibernating state, an energized state in the first operating state, and a sleep state in the second operating state, and detection means for detecting and storing data representing an amount/time log for drug expelled from the drug delivery device, the detection means having a sleep state in the hibernating state, and an energized state in the first and second operating states.

In other words, the device has a low-power hibernating state in which two functions (e.g. the detection and the communication means) are in a low-power sleep modus, a high-power state in which both of the functions (e.g. the detection and the communication means) are in an energized high-power state, and a medium-power state in which one function (e.g. the detection means) is in an energized high-power state and a second function (e.g. the communication means) are in a low-power sleep modus.

The state for the communication means may be changed from the energized to the sleep state when a first pre-set condition is met, e.g. (i) the communication means have unsuccessfully tried to establish wireless communication with a corresponding device for a predefined amount of time, (ii) the communication means have unsuccessfully tried to transmit an amount of data to a corresponding device for a predefined amount of time, (iii) the communication means have successfully transmitted an amount of data to a corresponding device, (iv) the first or second user-operatable means are actuated to set a dose respectively expel a set dose, or (v) the first or second user-operatable means are arranged in a parked position.

The state for the detection means may be changed from the energized to the sleep state when a second pre-set condition is met, e.g. (i) the second user-operatable means have been actuated to expel a set dose, (ii) the second user-operatable means have been actuated to expel a set dose and a predefined amount of time has lapsed, the amount of time allowing the electronic circuitry to display the amount of drug expelled, (iii) the second user-operatable means are arranged in a parked position, (iv) the second user-operatable means are arranged in a parked position and a predefined amount of time has lapsed, the amount of time allowing the electronic circuitry to display the amount of drug expelled, or (v) a predefined amount of time has lapsed.

In a further aspect a method of operating a drug delivery device is provided, comprising the steps of (i) providing a drug delivery device having a dose setting member and a wireless transmitter, (ii) energizing the wireless transmitter by moving the wireless transmitter to a first position, and (iii) de-energizing the wireless transmitter by moving the wireless transmitter to a second position.

As used herein, the term "medicament" is meant to encompass any medicament-containing flowable drug capable of being passed through a delivery means such as a hollow needle or cannula in a controlled manner, such as a liquid, solution, gel or fine suspension. Also lyophilized drugs which prior to administration are dissolved into a liquid form is encompassed by the above definition. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

DETAILED DESCRIPTION OF THE INVENTION

Figures 2, 3:
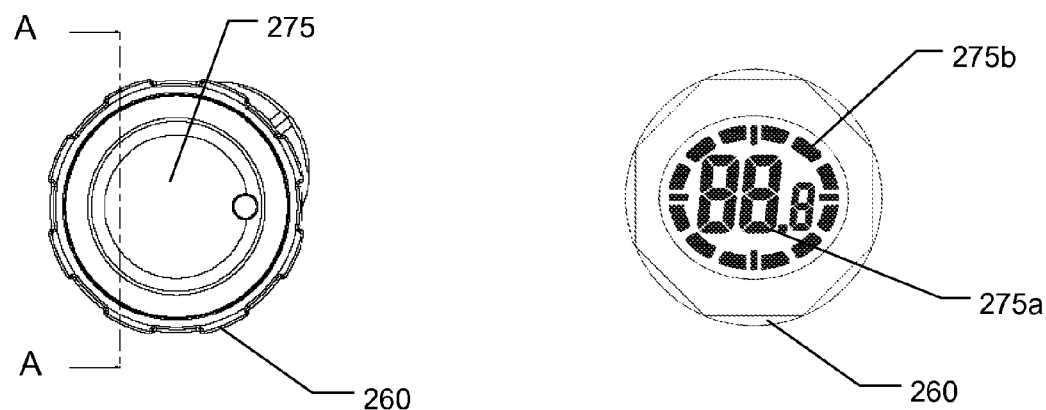
Figure 4A:
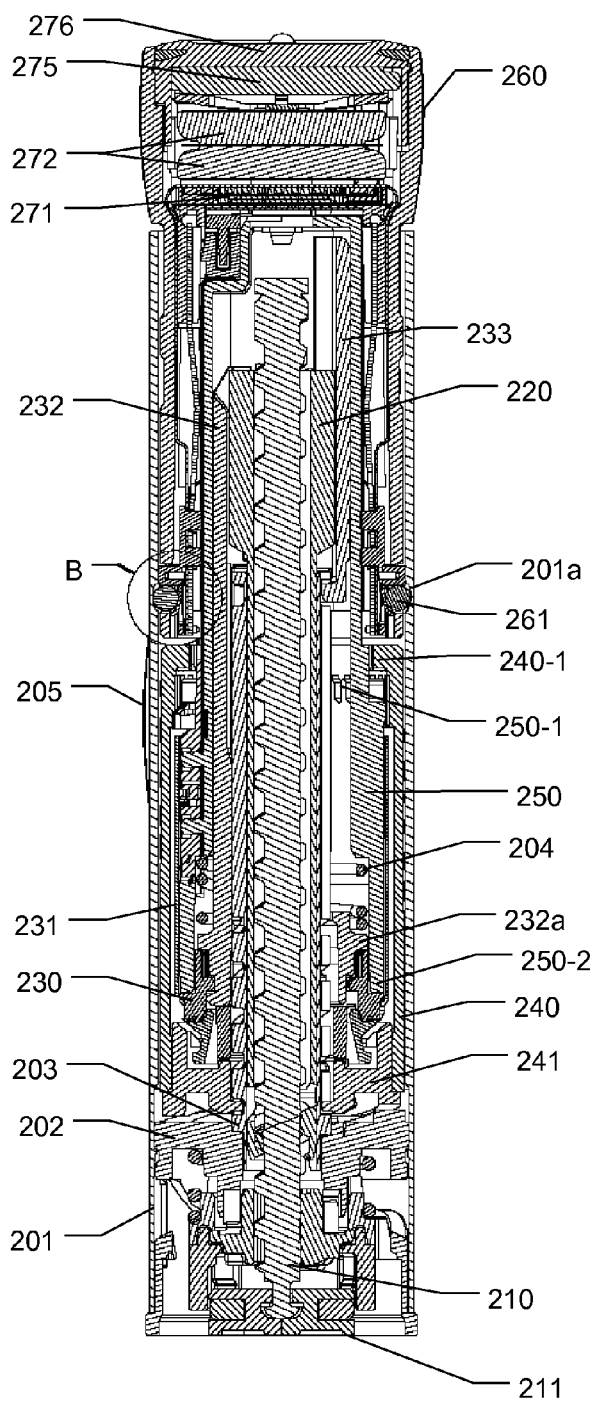
Figure 4B:
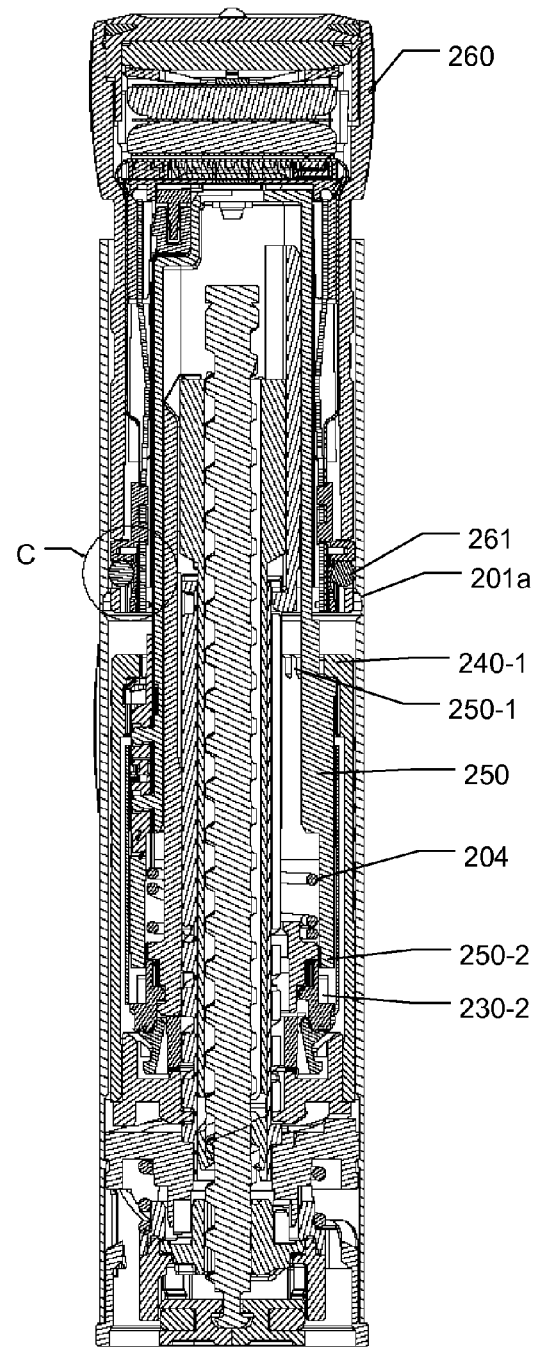
Figure 4C:
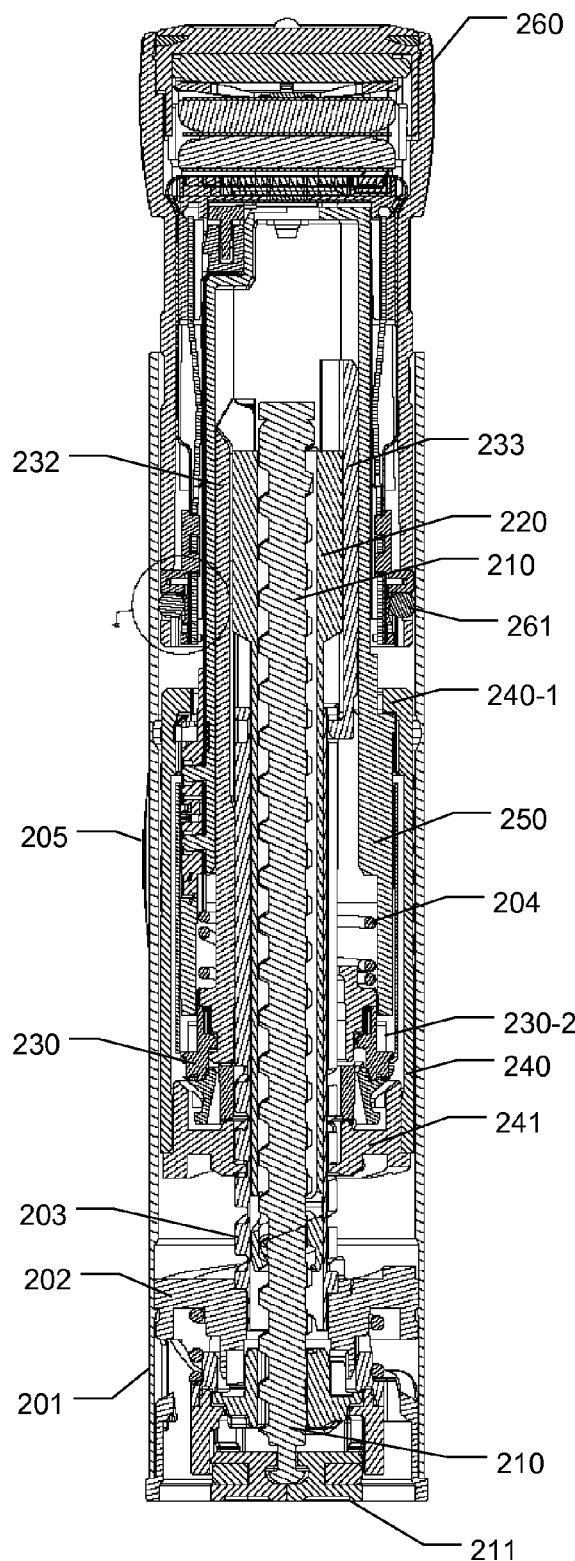
Figure 5:
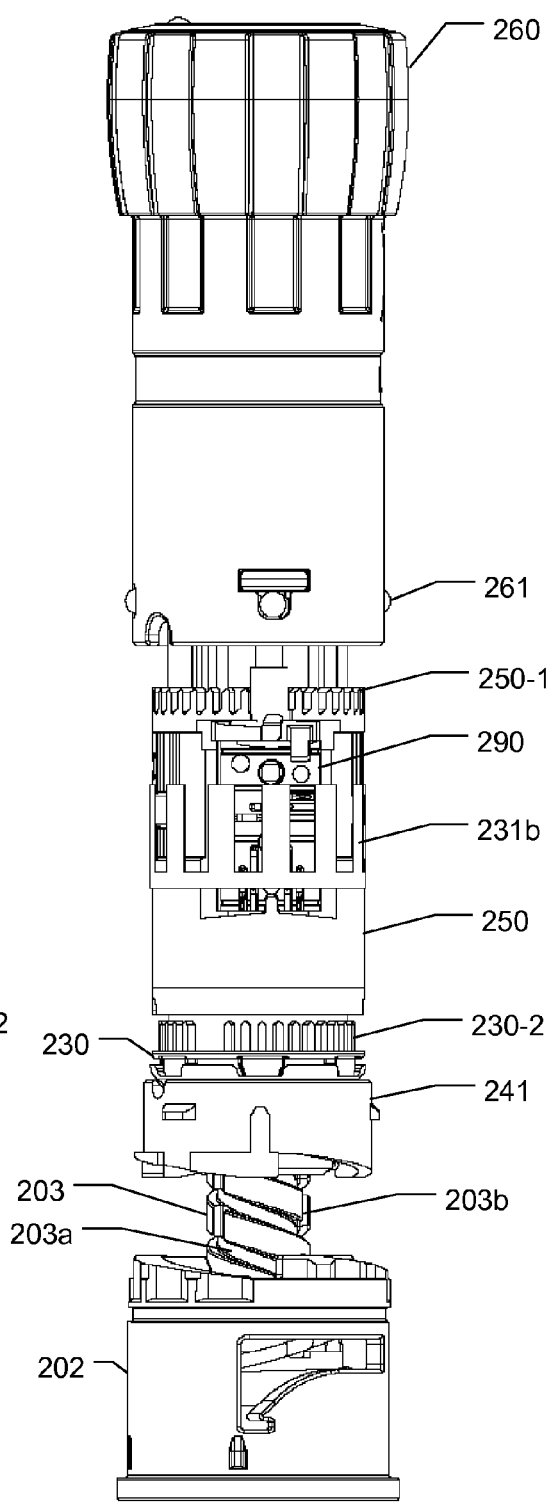
Figures 6A, 6B:
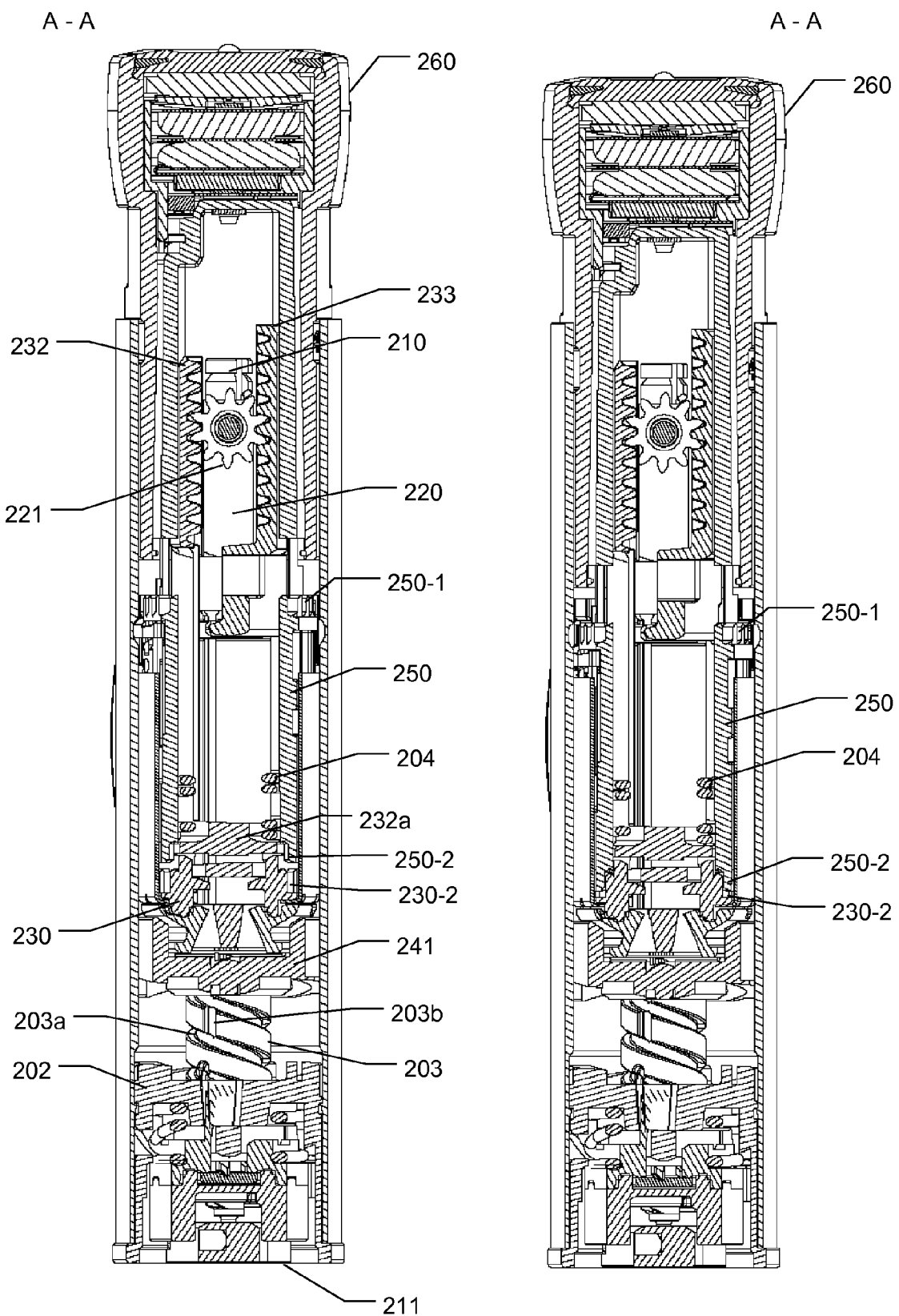
Figure 6C:
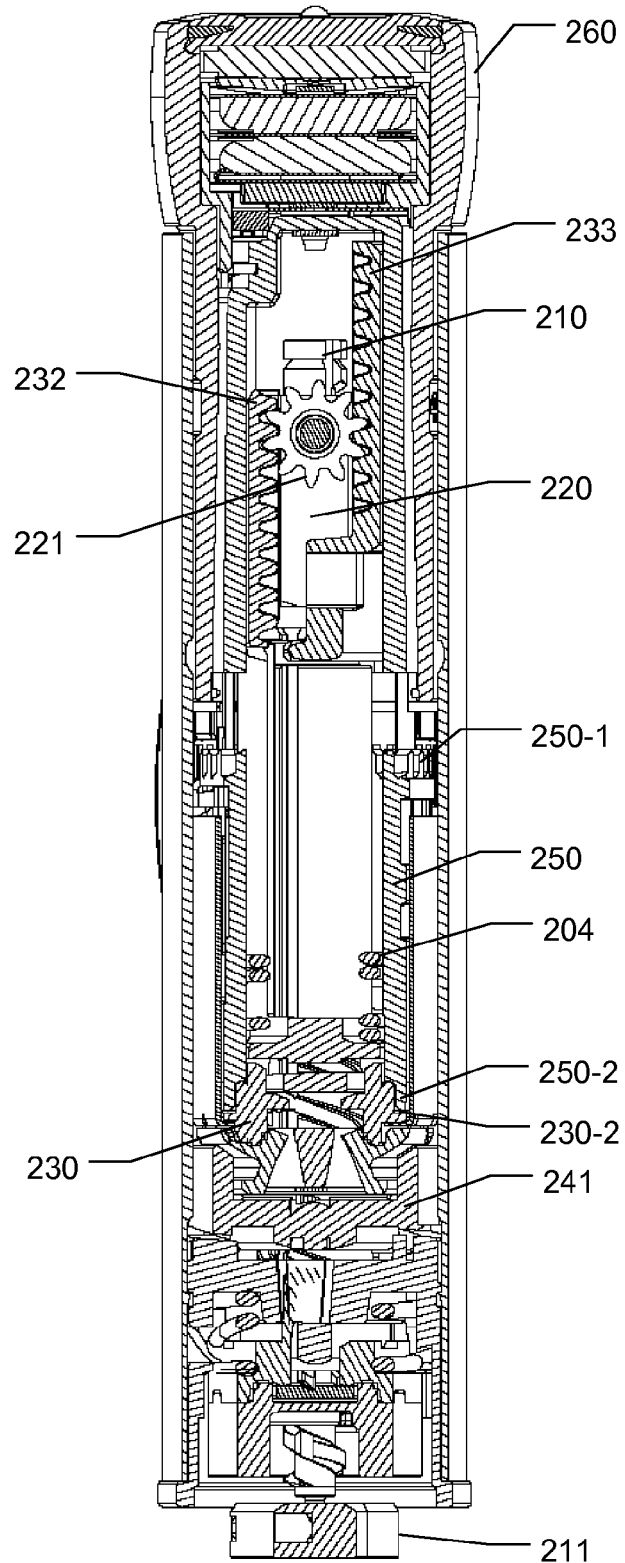
Figure 7A:
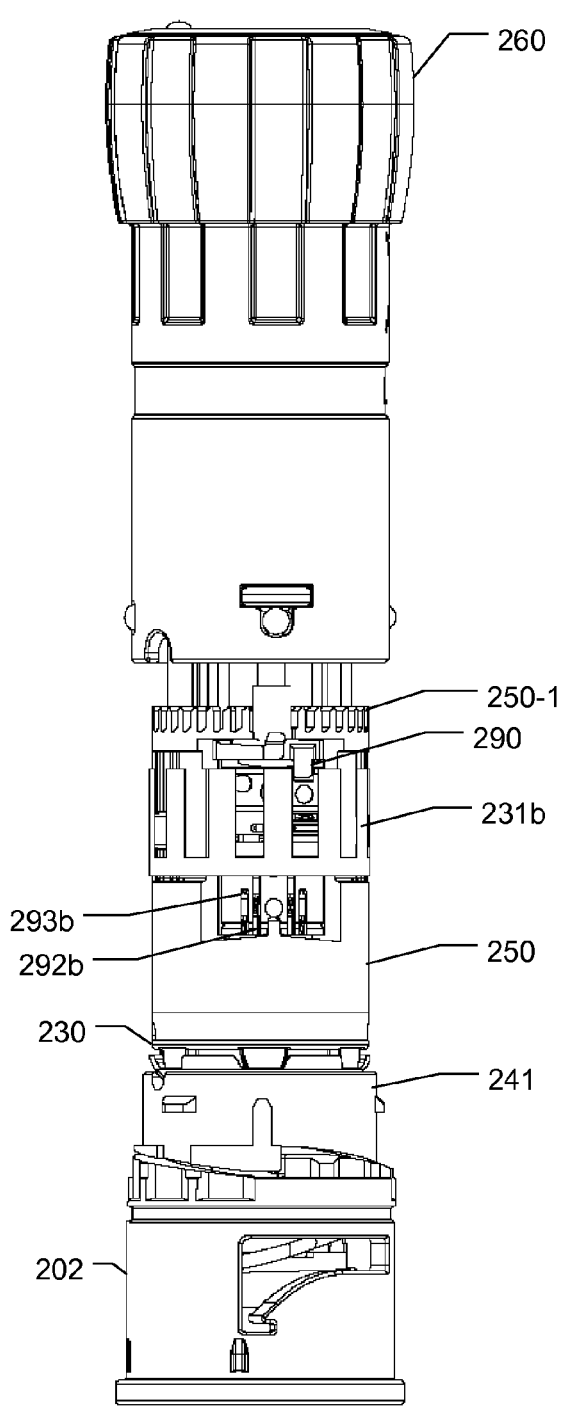
Figure 7B:
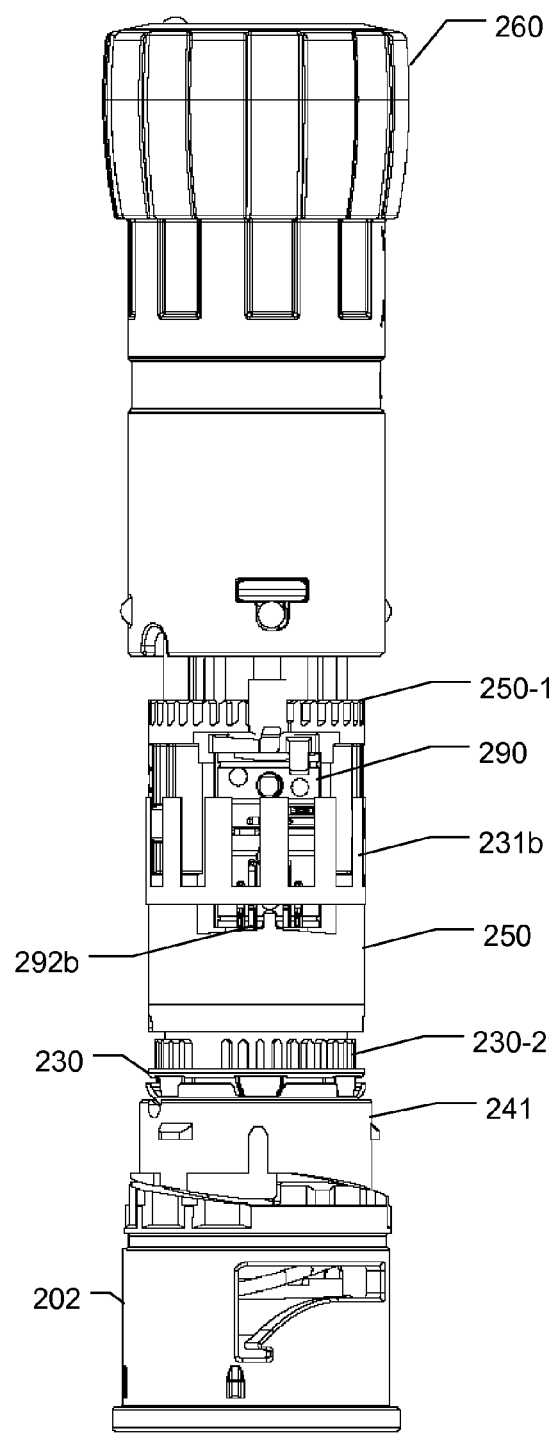
Figure 8:
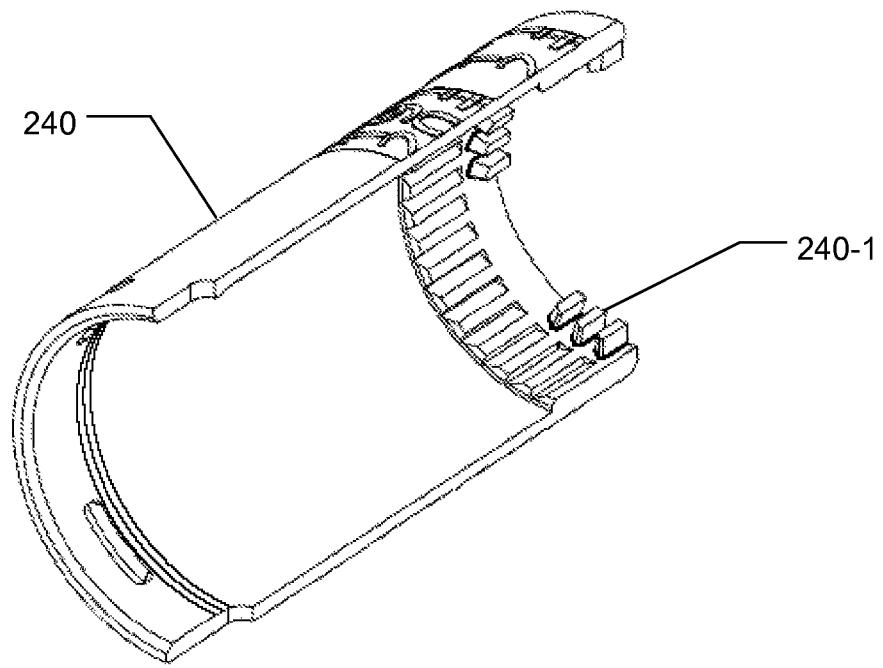
Figure 11:
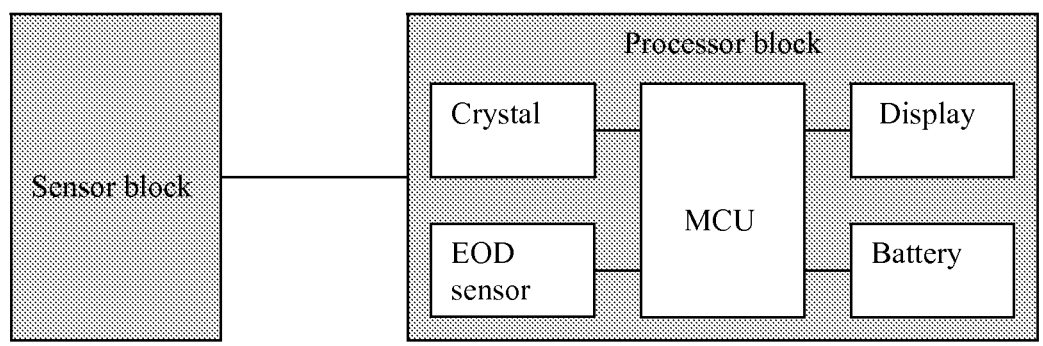
Figure 9:
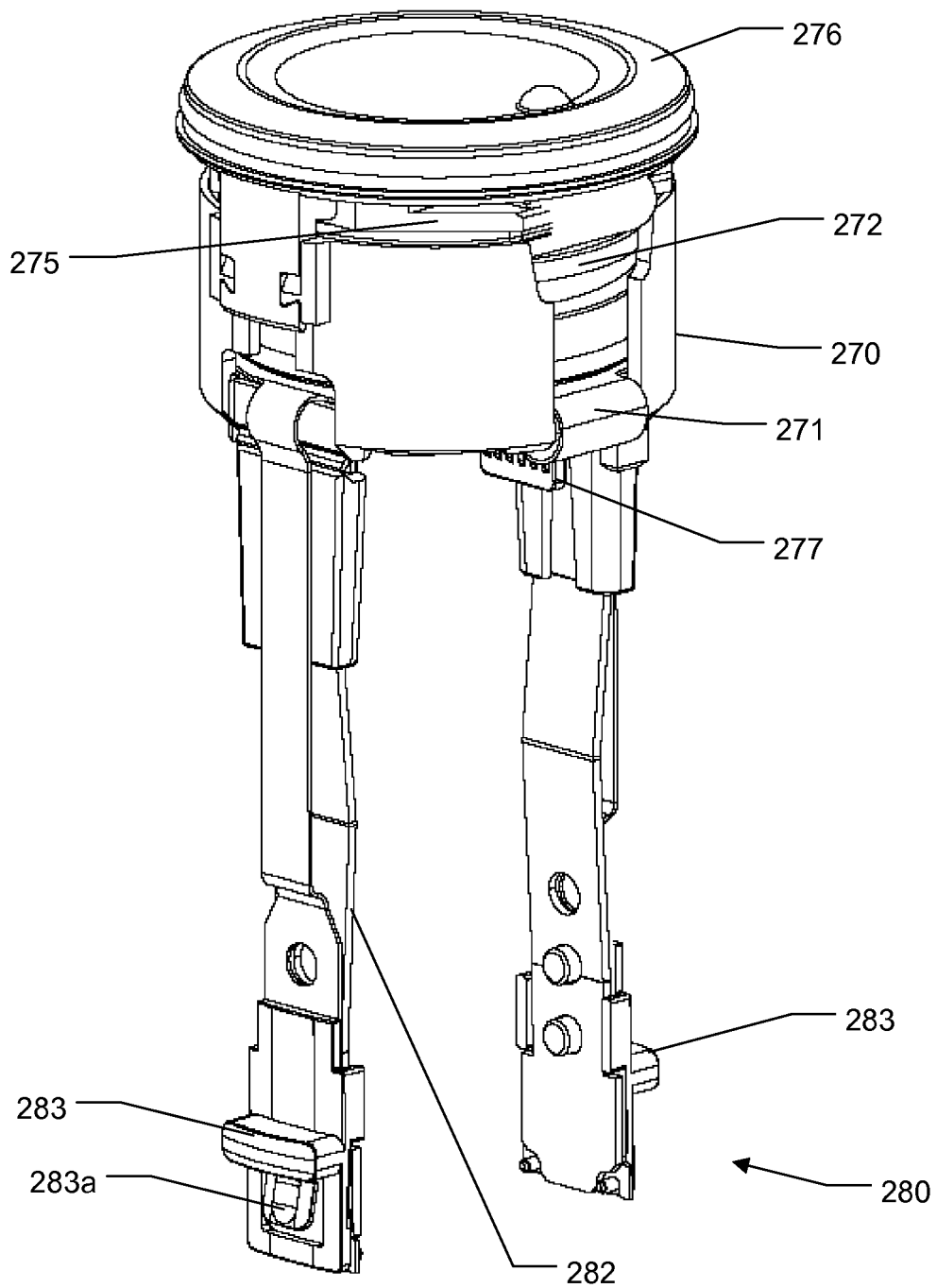
Figure 10:
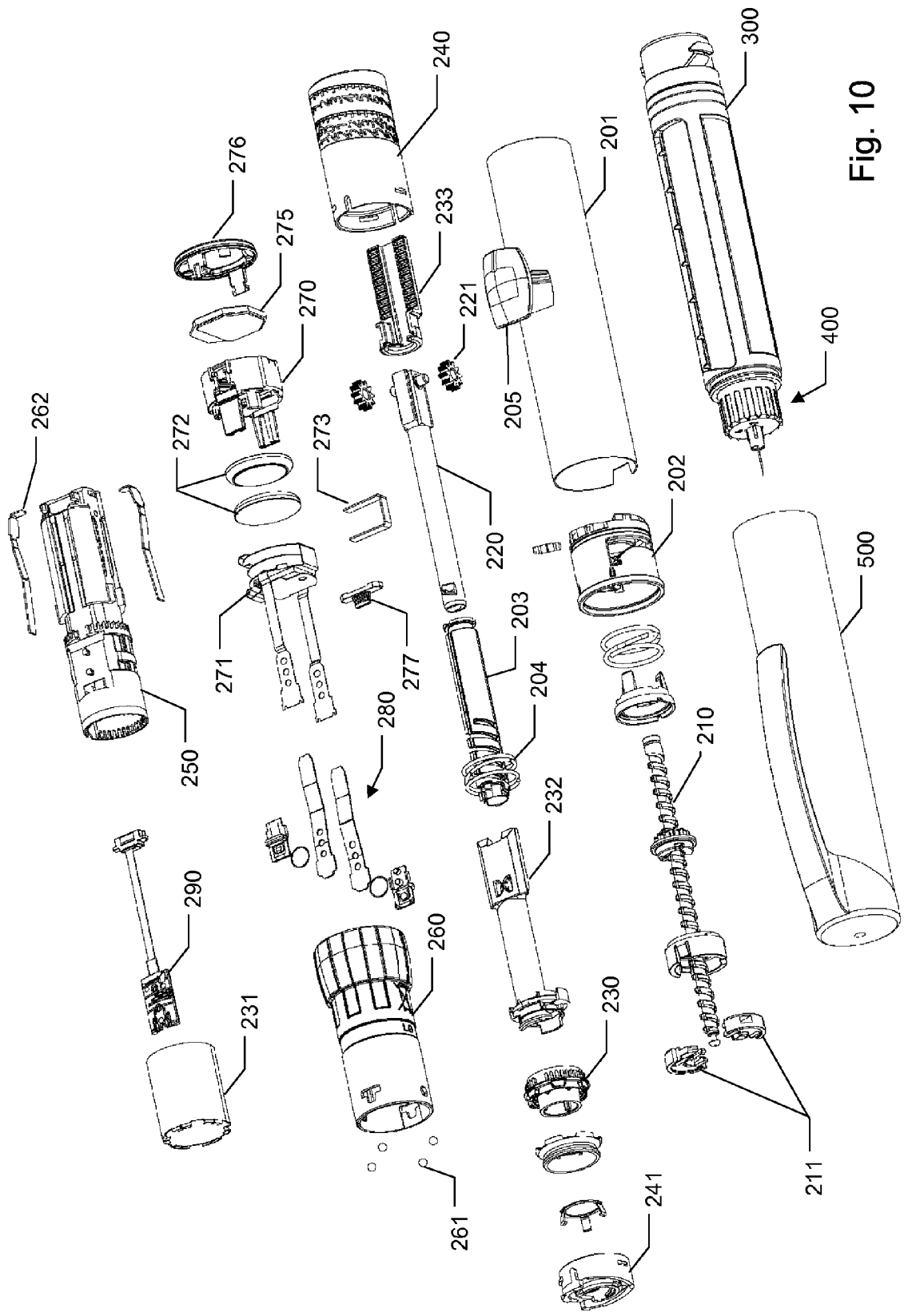

The invention will now be described in further detail with reference to the drawings in which:

FIG. 1 is a plan view of an injection device according to a first embodiment of the invention, FIG. 2 is a proximal end view of the injection device shown in FIG. 1, FIG. 3 is a proximal end view of the dosage selector display of the device shown in FIG. 1, FIG. 4*a* is a cross sectional view of dosing assembly with the dosage selector arranged in a parked position, FIG. 4*b* is a cross sectional view of dosing assembly with the dosage selector arranged in a ready position, FIG. 4*c* is a cross sectional view of dosing assembly with the dosage selector arranged at 18 IU, FIG. 5 is a side view of dosing assembly with the dosage selector arranged at 18 IU, FIG. 6*a* is a cross sectional view of dosing assembly in plane A-A as indicated in FIG. 2, dose setting mode, dosage selector arranged at 18 IU, FIG. 6*b* is a cross sectional view of dosing assembly in plane A-A as indicated in FIG. 2, dosage mode, initial position during injection, FIG. 6*c* is a cross sectional view of dosing assembly in plane A-A as indicated in FIG. 2, dosage mode, End-of-Dose, FIG. 7*a* is a side view of dosing assembly, same state as shown in FIG. 4*a*, FIG. 7*b* is a side view of dosing assembly, same state as shown in FIG. 4*b*, FIG. 8 is a perspective cross sectional view of the dose sleeve member, FIG. 9 is a perspective view of the stacked electronic components mounted in electronic module housing, FIG. 10 show an exploded perspective view of the injection device of FIG. 1, FIG. 11 is a block diagram of the electronics of the injection device of FIG. 1, FIGS. 12*a* and 12*b* is an enlarged view of the End-of-Dose switch shown in sections B and C of FIG. 4*a* and FIG. 4*b* respectively.

Figure 16:
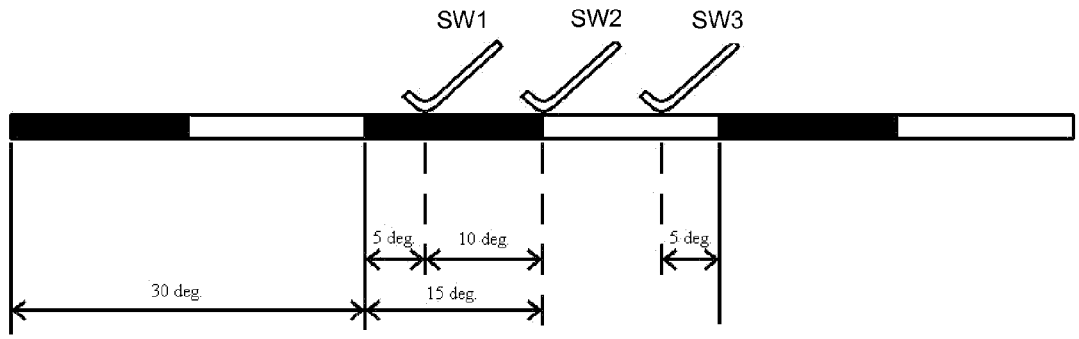
Figure 17:
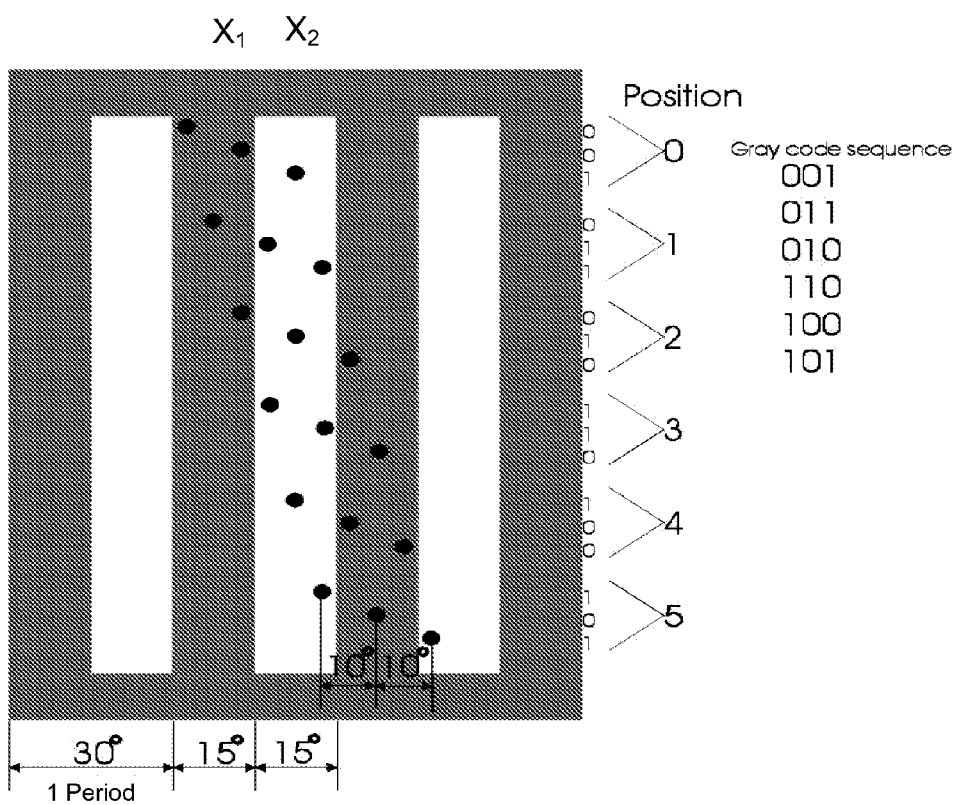
Figures 18, 19:
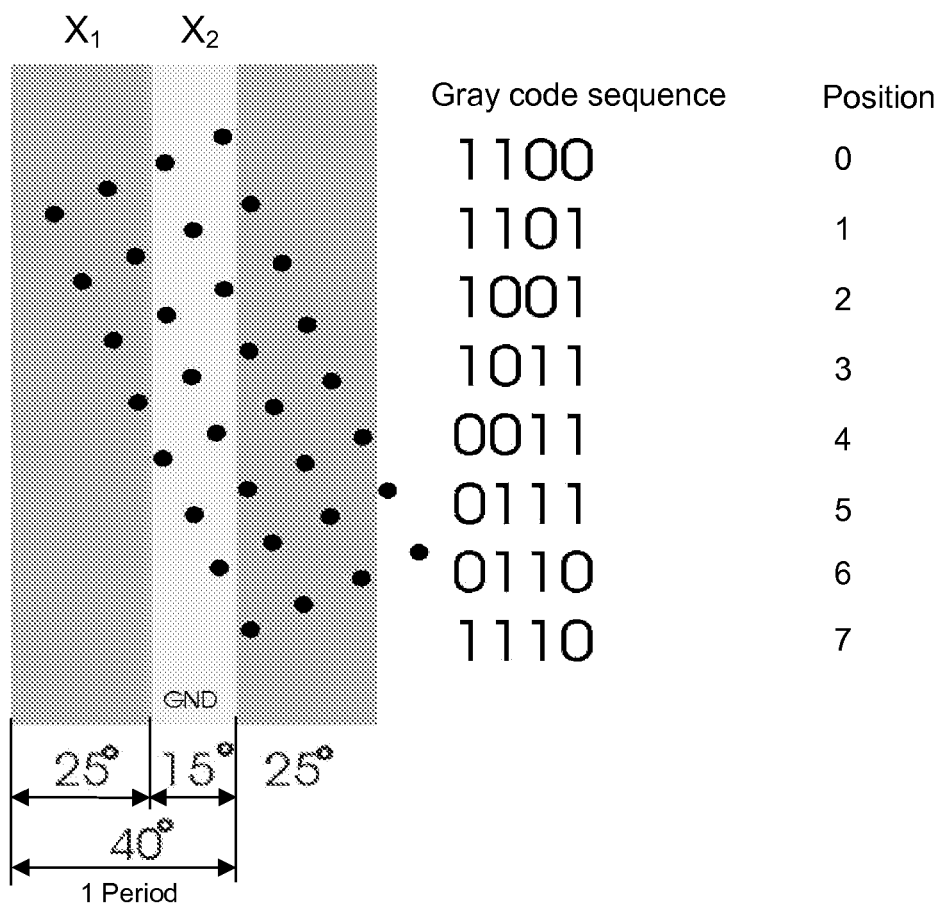
Figure 22A:
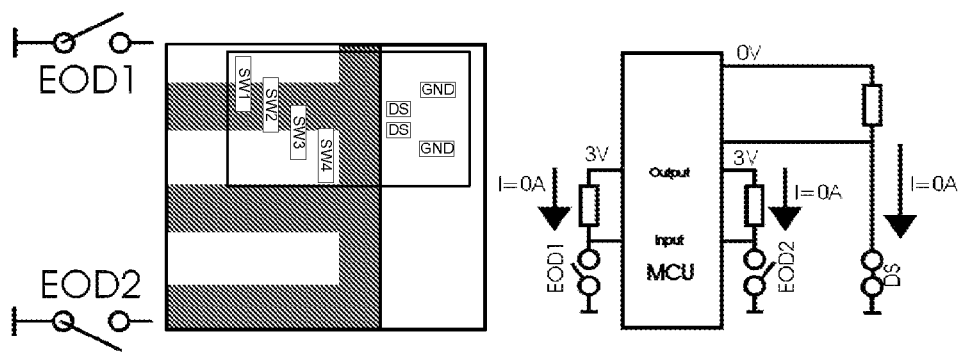
Figure 22B:
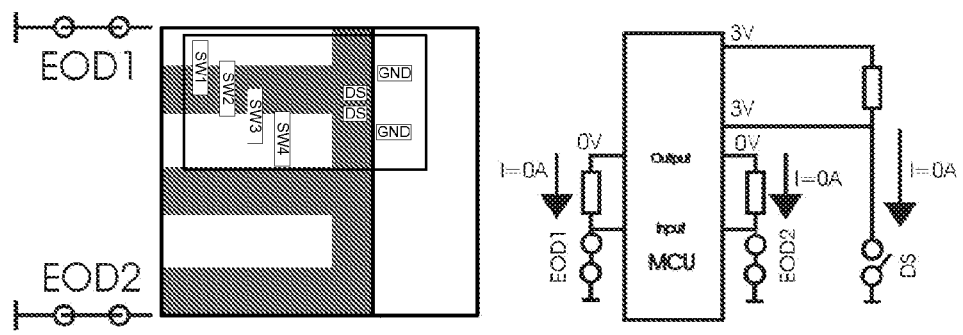
Figure 22C:
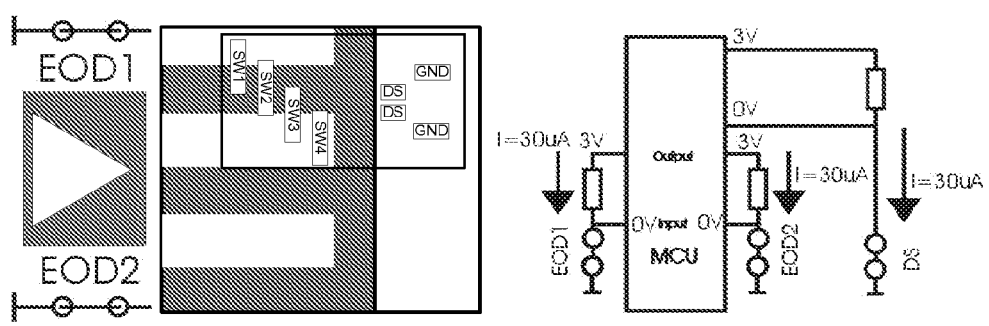
Figure 22D:
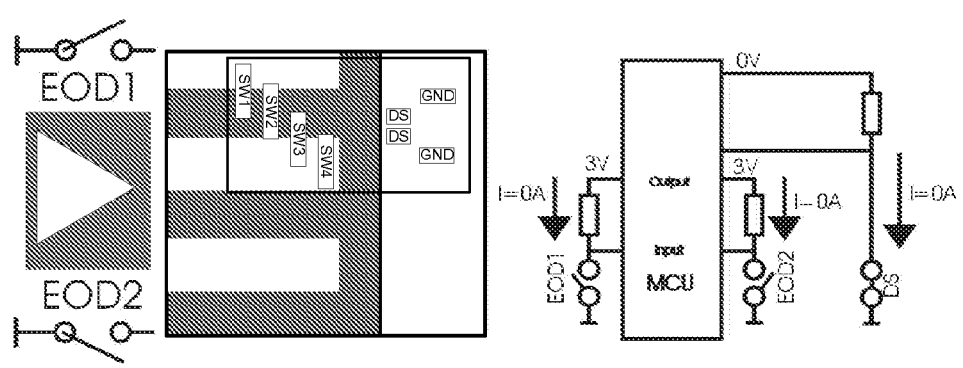
Figure 23A:
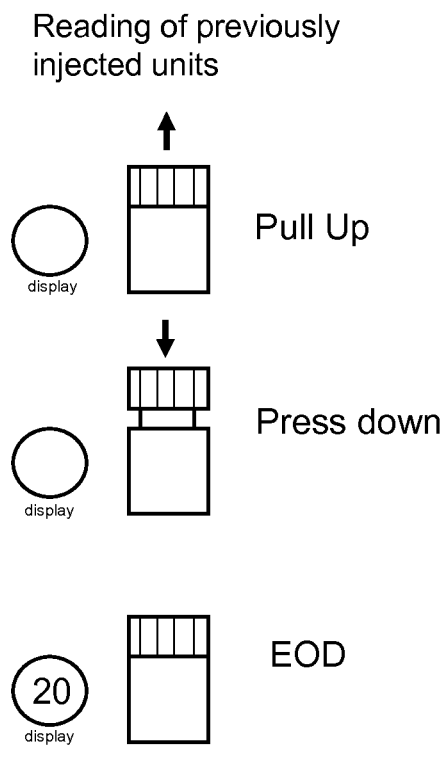
Figure 23B:
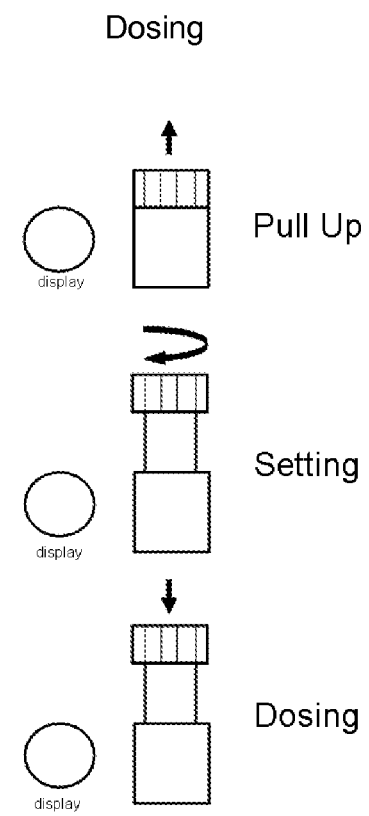
Figure 24:
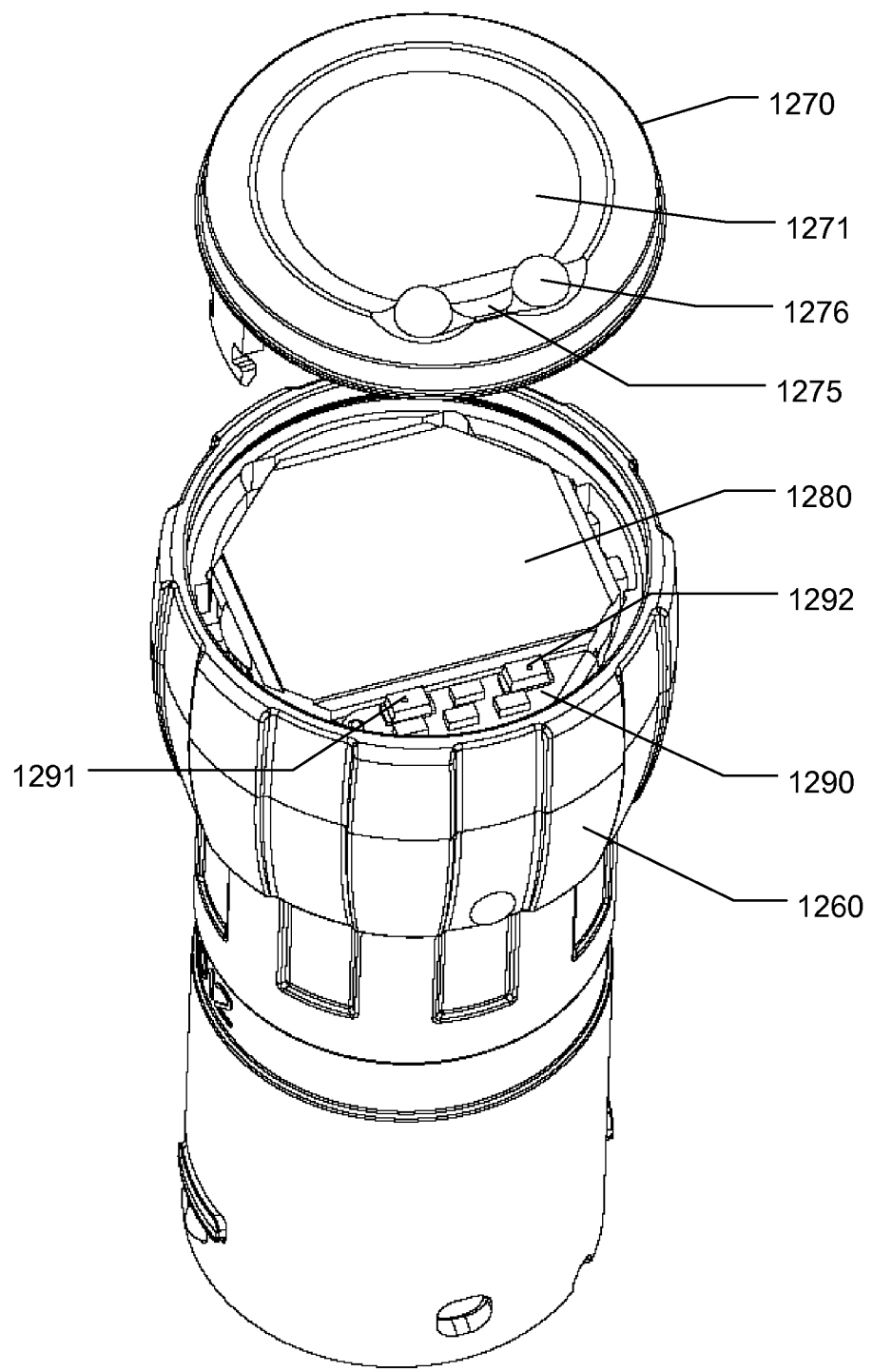

FIG. 13 is a detailed perspective view of a Gray code cylinder assembly,

FIG. 14 is a perspective view of a guide tube with a Gray code sensor assembly attached, FIG. 15 is a detailed perspective view of the Gray code sensor assembly, FIG. 16 is a schematic illustration of a first embodiment of the Gray code sensor in a particular position, FIG. 17 is a schematic illustration of the Gray code sensor of FIG. 16 shown at 6 different positions, FIG. 18 is a schematic illustration of a second embodiment of the Gray code sensor shown at 8 different positions, FIG. 19 is a table showing the possible Gray code bit patterns of the Gray code sensor shown in FIG. 18, FIGS. 20*a*, 20*b* show different switch configurations incorporating a pull-up resistor, FIG. 20*c* show a switch configuration according to an aspect of the present invention, FIG. 21 is a table showing signals of an injection device having EOD sensors and a sensor for sensing a dosing state FIGS. 22*a*-22*d* show different states of the electronic circuitry during operation of a device FIG. 23*a* is an illustration of the operating procedure for invoking the displaying of the previously injected dose, FIG. 23*b* is an illustration of the operating procedure during a normal administration procedure, and FIG. 24 shows a memory module of a second embodiment of the invention.

FIG. 1 generally show a medical delivery device in which the electronically assisted functions of the present invention finds application. The shown medical delivery device is a reusable injection pen generally designated 100 in which a medicament filled reservoir in the form of a cartridge may be accommodated in a cartridge retainer 300 which is coupled to the distal end of a dosing assembly 200. The dosing assembly 200 includes a mechanism for setting and expelling of doses of a medicament from a cartridge (not visible) held by cartridge retainer 300. The dosing assembly 200 include a user actuatable dosage selector 260 which may be manipulated for selecting a quantity of a dose and subsequently manipulated for injecting of the set dose through an injection needle assembly 400 shown attached to the cartridge retainer 300. Dosing assembly 200 further include a window 205 through which a mechanically based dose scale indicator can be viewed which displays particular selected dosage sizes which is set by the dosage selector 260. In the depicted form, during the dose setting process, dosage selector 260 is designed to be rotatable to set the dose, and when dosage selector 260 is so rotated to increase the selected dose, the dosage selector 260 translate out of dosing assembly 200 from the axial position shown in FIG. 1. During the dose injecting process which occurs after the dose setting process, when a plunging force is applied to dosage selector 260, dosage selector 260 is designed to be shifted to the left, and back to the axial position shown in FIG. 1, to cause the injecting mechanism components housed within the dosing assembly 200 to operate to cause the medicine in the cartridge to be injected.

FIG. 2 is an end view of the injection pen 100. The dosage selector 260 is provided with a memory module comprising an electronic display 275 which may be viewed at the proximal end face of the injection pen. FIG. 3 shows the electronic display 275 of a particular embodiment of the device wherein dosage sizes may be read at display are 275a and the time lapsed since the last performed injection may be viewed at display area 275b. In the shown embodiment, the time since last injection may be indicated as seconds lapsed since the finalization of an injection, indicating needle insertion waiting time subsequent to completion of an injection movement, or hours lapsed since the injection. Hence, the number of segments displayed in display area 275b provides a quick reference to the time lapsed since the last injection, either as hours elapsed or seconds elapsed. In particular embodiments a plurality of previously stored expelled dosage sizes along with timing information are stored as data sets and may be shown on display 275 by sequentially operating the dosage selector 260, e.g. by axially moving the dosage selector back and forth or alternatively by rotating the dosage selector.

FIG. 4a is a cross sectional view of dosing assembly 200 shown in a state where the dosage selector 260 has been arranged in a parked position, i.e. fully pushed in. Typically the pen enters this state after a complete injection of a previously set dosage (in the following referred to as End-Of-Dose or "EOD"). FIG. 4b is a cross sectional view of the dosing assembly 200 in a state where the dosage selector 260 has been pulled slightly in the proximal direction (in the following referred to as dose setting mode) and where the dosage selector 260 enters the dose adjusting position referring to 0 IU. FIG. 4c is a cross sectional view of the dosing assembly (still in dose setting mode) where the dosage selector has been dialled into a particular dose adjusting position referring to a dose size of 18 IU.

The mechanical design of dosing assembly 200 closely relate to the pen designs shown in WO 01/95959, the cited document being incorporated by reference. All components of the exemplary embodiment of the present invention are shown on FIG. 10 which shows an exploded perspective view of the injection device 100.

Dosing assembly 200 comprises a housing which includes a cylindrical housing sleeve 201 which permanently connects to base bushing 202 and further permanently connects to a base 203. Base 203 is formed as a cylindrical member arranged coaxially and internally within sleeve 201. Dosing assembly 200 further comprises a plunger stem in the form of a piston rod 210 extending through the distal part of dosing assembly 200. Attached to piston rod 210 is a piston washer 211 adapted to cooperate with a piston in a cartridge accommodated in cartridge retainer 300 so as to force the piston forward in the cartridge for expelling fluid held in the cartridge.

A distal portion of the dosing assembly 200 includes a rotary lock mechanism for rotatively locking the piston rod 210 relative to the base bushing 202 so that during the injection procedure, the piston rod will only be allowed to move axially and not rotationally. However, the rotary lock mechanism allows for the rotary lock to be released during cartridge replacement. As this type of mechanism is well known in the art, it will not be described further. In alternative configurations, the rotary lock mechanism in conjunction with the piston rod acts as a rotational guide which induces a rotational movement of the piston rod in the course of the injection procedure such as disclosed in WO 2006/114395.

Along the length of the piston rod 210 a thread is provided along its exterior surface. Dosage tube 220 encircles piston rod 210 and acts as a driver for driving the piston rod forward during the expelling procedure. The piston rod outer thread couples to an internal thread formed in the distal portion of the dosage tube 220.

The dosing assembly 200 include a gearing arrangement for providing a mechanical advantage between relative axial movements of the dosage selector 260 with respect to the dosage tube 220. In the depicted embodiment, the gearing is provided by a gearing mechanism incorporating toothed racks and gearwheels. The gearing arrangement will be discussed later with reference to FIGS. 6a to 6c.

Base 203 includes on its outer surface a coarse thread 203a (best shown on FIG. 5). A dose sleeve member 240 formed as a cylindrical barrel encircles base 203. Dose sleeve member 240 is in the depicted embodiment provided with a scale in the form of helically arranged numbers printed on the exterior surface of the dose sleeve member so as to provide a mechanical dose scale indicator. Dose sleeve member 240 is snapped into engagement with dose sleeve thread member 241 which includes an internal thread adapted to cooperate with the thread 203a formed on the exterior surface of base 203. During operation of the injection pen, as the dose sleeve member 240 is rotated, consecutive dose scale numbers appear beneath window 205. Hence, the particular dose amount which has been set can be read from the exterior of the pen.

Dosage selector 260 connects to axially extending guidance tube 250. In the assembled form of the dosing assembly, dosage selector 260 snaps into fixed engagement with guidance tube 250. Guidance tube 250 is rotationally fixed relative to dosage tube 220 but is allowed to move axially with respect to dosage tube 220. Guidance tube 250 performs as a mode selector between two pen modes: a) dose setting mode and b) dosage mode. In dose setting mode, guidance tube 250 performs as a member for adjusting the particular dose by turning the dosage tube relative to the piston rod. It also performs as a member for transferring rotational movements of the dosage selector 260 during dose setting to the dose sleeve member 240. In dosage mode guidance tube 250 performs as a member for transferring axial movements of the dosage selector to axial movements of the dosage tube via the above mentioned gearing arrangement.

Guidance tube 250 is provided with two sets of coupling teeth 250-1 and 250-2. The first set of coupling teeth 250-1 extend in the proximal direction and are adapted to engage distally extending cooperating coupling teeth 240-1 formed on the interior surface of dose sleeve member 240 (best seen in FIG. 8). The second set of coupling teeth 250-2 are positioned at the most distal end of guidance tube 250 and extend in the distal direction. The coupling teeth 250-2 will be described in detail further below. As guidance tube 250 is able to translate a short distance in the axial direction relative to dose sleeve member 240, the coupling teeth 250-1 and 240-1 may be coupled into and out of engagement with each other. Hence, the coupling teeth 250-1 and 240-1 forms a dose dialling clutch for releasably engaging the guidance tube 250 with the dose sleeve member 240. In the depicted state shown in FIG. 4a which shows the pen in dosage mode the dose dialling clutch is disengaged. In the state shown in FIG. 4b which shows the pen in dosage mode, the dosage selector has been pulled a slight distance away from the pen housing. In this state, guidance tube 250 is shifted slightly in the proximal direction so that the coupling teeth 250-1 engages the coupling teeth 240-1 of the dose sleeve member 240. In this state the dose sleeve member 240 follows rotation of the dosage selector 260.

Turning again to FIGS. 4a and 4b, dosing assembly 200 includes a toothed rim 230 arranged coaxially with respect to base 203 and arranged proximally with respect to dose sleeve thread member 241. Toothed rim 230 includes a plurality of inwardly directed protrusions each of which cooperates with axially extending tracks 203b formed in the exterior surface of base 203 (see FIG. 5). Hence, toothed rim 230 may be moved axially but cannot rotate with respect to the housing. Toothed rim 230 further include a set of proximally facing coupling teeth 230-2 (see FIG. 4b) arranged to releasably engage the above mentioned second set of coupling teeth 250-2 of guidance member 250. In dosage mode, as depicted in FIG. 4a, the coupling teeth 230-2 and 250-2 are engaged and hence guidance member 250 is prevented from rotating (coupling teeth 230-2 not visible in FIG. 4a). In dose setting mode, as shown in FIG. 4b, the coupling teeth 230-2 and 250-2 are disengaged. In this mode, the guidance member may be rotated and moves axially in accordance with the movement of the dose sleeve thread member 241 climbing the coarse thread 203a of the base 203 as the dosage selector is rotated.

As shown in FIG. 4c, the dosage selector 260 has been turned a complete revolution, which in the depicted embodiment correspond to a dose volume of 18 IU. Further turning of the dosage selector 260 is possible until a max dose is reached (in this case 1 complete revolution+⅔ fractional revolutions corresponding to 30 IU). If the dosage selector has been adjusted into a dose size larger than the intended, a decrease of dose sized can be accomplished by turning the dosage selector in the opposite direction until the desired dose size is shown in window 205. The movement of the dosage selector 260 is preferably carried out in discrete steps of half unit or full unit increments. The depicted embodiment comprises a click mechanism (not shown) provided by features associated with the toothed rim 230 and the distal section of displaceable rack 232 (displaceable rack described in detail further below). In the depicted embodiment, the click mechanism provides 36 distinct positions for each complete revolution that the dosage selector 260 undergoes during dose setting.

FIGS. 4a, 4b and 4c further shows a toothed base rack 233 which is attached to the proximal end of base 203 so that it cannot be shifted along the central axis of the pen but can be journaled around the central axis of the pen in accordance with the rotation of the guidance member 250. Also shown is a toothed displaceable rack 232 which lies opposite the base rack 233 and which extends in the distal direction towards the toothed rim 230. The distal section of displaceable rack 232 forms a cylindrical part 232a which is arranged to encircle base 203 so that displaceable rack 232 can be moved axially and rotationally with respect to the base 203. In the assembled state of the dosing assembly, the cylindrical part 232a of the displaceable rack 232 is positioned adjacent the toothed rim 230 which again is positioned next to the dose sleeve thread member 241. As indicated in the drawings, intermediate elements are arranged between toothed rim 230 and dose sleeve thread member 241 in order to maintain the toothed rim 230 and the dose sleeve thread member 241 axially next to each other while allowing relative rotation.

FIGS. 4a, 4b and 4c further shows a spring member 204 arranged between a distal face of the guidance tube 250 and a proximal face of the cylindrical part 232a of the displaceable rack. Spring member serves to urge the guidance tube 250 in the proximal direction towards the state referred to above as the dose setting mode. However in the EOD state as shown in FIG. 4a, a ball lock mechanism acts to retain the pen in the EOD state until the user pulls the dosage selector 260 into dose setting mode as shown in FIG. 4b. The ball lock mechanism comprises 4 balls 261 arranged 90 degrees apart along the circumference of the dosage selector by accommodating the balls 261 in corresponding cutouts formed in the wall section of dosage selector 260 (see also FIG. 5). Leaf springs members 262, 282 are arranged at interior wall sections of the dosage selector 260 and used to urge each of the balls radially outwards. In the EOD state shown in FIG. 4a the balls are axially aligned with an annular recessed channel 201a formed in the interior wall surface of the housing sleeve 201. In this state, the balls are moved into the annular channel 201a and the force of the leaf springs 262, 282 serves to maintain the dosage selector in this position and provides a reluctance against unintentional release of the dosage selector away from the EOD state. As noted above, a proximally directed force exerted on the dosage selector 260 will release the balls 261 from the annular channel and spring member 240 serves to put the pen into dose setting mode, as shown in FIG. 4. It is to be noted that two of the balls 261 serves as additional electrical switching functionality for sensing the EOD state. This will be described in detail further below.

FIGS. 4a, 4b and 4c further shows electronic components for facilitating the electronic features of the injection device which will be described further below. The components which are shown include a main circuit which in the following will be designated as an electronic module 271, two electrical cells 272 for powering the electronic module and an electronic display 275. A display window 276 is arranged at the proximal face of the dosage selector 260 to facilitate inspection of electronic display 275. A Gray code cylinder 231 is fixedly attached to toothed rim 230 extending in a proximal direction from toothed rim 230 whereby it partially encircles the guidance tube 250. Gray code cylinder 231 is in more detail shown in FIG. 13. In the shown embodiment, Gray code cylinder 231 is part of a sensor system for detecting movements between guidance tube 250 and toothed rim 230. The Gray code cylinder 231 comprises a cylindrical sleeve 231a made of an electrical conducting material and a layer of electrically insulating material arranged as a pattern 231b on the interior surface of the cylindrical sleeve 231a. The pattern 231b of electrically insulating material is formed as a series of axially extending bars which are repeated all the way around internally in the cylinder. The axial bars connect to a circumferential continuous band at the distal end of the bars.

FIG. 5 is a side view of the dosing assembly in the same state as shown in FIG. 4c (dose setting mode, dose size of a couple of 18 IU being set). In the drawing, in order to visualize particular components of the device, the housing sleeve 201 and the dose sleeve member 240 have been omitted. Likewise, the cylindrical sleeve 231a of the Gray code cylinder is omitted but the electrically insulating pattern 231b is visible. A Gray code sensor assembly 290 is fixed to an exterior surface of the guidance tube 250 so as to axially overlap with the Gray code cylinder 231. Gray code sensor assembly comprises a number of contact springs arranged to galvanically contact the Gray code cylinder so as to facilitate contact reading of the grey code cylinder. In combination the contact springs and the grey code cylinder performs as a number of distinct switches which connects to electronic module 271.

FIGS. 6a, 6b and 6c are cross sectional views of the dosing assembly in a plane A-A as indicated in FIG. 2. In these drawings the dose sleeve member 240 has been omitted for improving clarity. The drawings 6a, 6b and 6c primarily serve as illustrating the injection procedure.

FIG. 6a shows the dosing assembly 200 in a state corresponding to the state shown in FIGS. 4c and 5 (dose setting mode, dose size of 18 IU being set). In this state the coupling teeth 240-1 of the dose sleeve member 240 (not shown) engages the coupling teeth 250-1 of the guidance tube 250 so as to transfer rotational movement from the dosage selector 260 to the dose sleeve member 240. As the second set of coupling teeth 250-2 do not engage the set of coupling teeth 230-2 of the toothed rim 230, the dosage selector 260 is allowed to rotate. In FIG. 6, base rack 233 which is axially fixed in the device and displaceable rack 232 connects via gear wheels 221. The centre of each gear wheel 221 is coupled to shaft parts arranged to extend from the dosage tube 220 in a direction perpendicular to the central axis of the device so as to allow the wheels for journaled movement on the shafts. This arrangement serves as a 2:1 gearing between axial movements of the displaceable rack and axial movements of the dosage tube 220.

In FIG. 6b, during the initial stage of the injection procedure, the state of the injection device changes to dosage mode. During the initial stage of pushing the dosage selector 260, the guidance tube 250 shifts slightly in the distal direction against the bias of the spring member 204 which compresses. Due to the slight distal shift in position of the guidance tube 250, the first set of coupling teeth 250-1 of the guidance tube 250 moves out of engagement with the coupling teeth 240-1 of the dose sleeve member 240. Again, due to the slight distal shift of guidance tube 250, the second set of coupling teeth 250-2 engages the coupling teeth 230-2 of the toothed rim which serves as a rotational lock of the guidance tube. Hence, in dosage mode, the dosage selector 260 is prevented from rotating and thus the dose size which has been previously selected cannot be changed during the progression of the injection. In the shown device, when the guidance tube 250 is positioned in intermediate positions between the dose setting mode and the dosage mode, both sets of couplings are engaged. Thus, there will be no intermediate positions where both of the two couplings are disengaged simultaneously.

Continued force exerted on the dosage selector 260 in the distal direction is transferred via guidance tube 250 and spring member 204 to the stacked components: cylindrical part 232a of the displaceable rack, toothed rim 230 and sleeve thread member 241. As the sleeve thread member 241 moves along the thread 203a, the sleeve member 240 rotates and moves in the distal direction. As the cylindrical part 232a of the displacable rack 232 is likewise moved distally, the movement of the displaceable rack 232 induces a movement of the dose setting member 220 via the gear transmission.

In FIG. 6c, which shows the dosing assembly when the injection procedure has finalized, the device is still in dosage mode but in the EOD state. By comparing FIGS. 6b and 6c, it is readily apparent that the gearing mechanism provides a 2:1 gearing between the axial displacement of the dosage selector 260 and the piston washer 211 attached to piston rod 210. Also it will be recognized that the return movement of the sleeve member 240 is synchronized with the movement of the piston rod 210 so that the dose size numbers shown in window 205 at all times indicates the dose remaining to be injected during injection.

FIGS. 7a and 7b show similar views as the one shown in FIG. 5. In FIGS. 7a and 7b the same components, that is the housing sleeve 201, the dose sleeve member 240 and the cylindrical sleeve 231a have been removed for improving intelligibility. FIG. 7a shows the device in the parked position, i.e. in the EOD state. FIG. 7b show the device in the ready position where the device has been positioned in the dose setting position corresponding to 0 IU. These states correspond to the states shown in FIGS. 4a and 4b respectively.

Turning now to the electronics of the present invention, the injection device comprises an electronic detection system for monitoring different states of the device and for detecting the size of expelled doses of the medicament held in the cartridge. The electronics provides the user with information in respect of the last delivered dose (amount and time since delivery). Referring to FIG. 10 the device comprises an electronic module generally referred to as 271 which includes a folded PCB, a processor and various other electronic components. The folded PCB of electronic module 271 extends in two legs which combine with additional components to form two EOD switches (generally referred to as 280). Electronic module 271 further connects to a sensor assembly, below designated Gray code sensor assembly 290 which serves for detecting movements of the guidance tube 250. The electronics module 271 is further connected to two electric cells 272 which are sandwiched between parts of the folded PCB, the cells being connected in parallel while being mechanically mirrored. A battery clip 273 made of spring metal serves to maintain the electric cells and the flexible print in secure galvanic contact. The stacked configuration ensure that at least one electric cell is kept in galvanic contact with the electronic module even during mechanical impacts. On top of the electronic cells 272, display 275 connects to the electronic module 271 by means of the folded PCB.

The above mentioned components are configured in a stacked configuration which is mounted in electronic module housing 270 and a memory display window 276 closes off the stacked components. In the assembled state, the electronic module housing 270 is mounted in the dosage selector 260 so that memory display window 276 constitutes the proximal end face of dosage selector 260. In the described embodiment, the memory display window 276 is provided with a seal which surrounds the peripheral part to seal the junction to the dosage selector 260, which seal may be formed by co-molding during the molding process of display window 276. FIG. 9 is a perspective view of the stacked electronic components mounted in electronic module housing 270 in a well type configuration. Below the electronics module housing 270 two legs of the folded PCB of electronic module 271 extend in the distal direction of the dosing assembly towards the ball lock mechanism previously described. A connector 277 provides a connectible interface to the Gray code sensor assembly 290 which includes a mating connector. To reduce unnecessary use of power, one or both of the battery terminals are connected to the electronic circuitry through the connector of the Gray code sensor assembly module interface connector. Hence, battery consumption is deferred until assembly of the Gray code sensor assembly 290 onto the electronic module 271.

Referring to the block diagram of FIG. 11 the electronic module comprise a processor (MCU) powered by a battery and crystal is used to generate the low-speed clock needed for the processor and the real-time clock which is used for signalling time lapsed since last injection. The processor further includes circuitry for controlling readout of the electronic display. During manufacture, the stacked configuration of FIG. 9 is assembled as a single finalized unit which can be tested prior to assembling with the remaining parts of the dosing assembly. In this state no power are drawn from the batteries before the electronic module 271 and the Gray code sensor assembly 290 are connected.

FIGS. 12a and 12b shows magnified views of the indicated section B and C shown in FIGS. 4a and 4b respectively. The drawings depicts the above described ball lock mechanism which serves as a retaining mechanism when the dosage selector 260 is in EOD position. As mentioned earlier, two of the four ball lock mechanisms are provided with additional functionality for electronically sensing whether the dosage selector 260 is in EOD or not. The two types of ball lock mechanisms are arranged as opposed pairs shifted 90 degrees apart. In FIG. 12a, which show the state at EOD, the ball 261 is positioned radially outwards in the recessed annular channel 201a. The EOD switch 280 comprises a spacer 283 which is sandwiched between the guidance tube 250 and the housing sleeve 201. Spacer 283 provides a well defined mutual distance between the guidance tube 250 and the internal wall section of housing sleeve 201. The spacer mounts on spring member 282 which is a leaf spring forcing the spacer 283 radially outwards. The spring member 282 additionally serves as a switch base upon which the remainder of the switch components are mounted. As shown in FIG. 12a a part 271b of the folding PCB of electronic module 271 is mounted "on top" of spring member 282 (shown to the left in the drawing). Folding PCB includes contact electrodes which are adapted to be short-circuited by switch dome 281 when the switch is activated (see FIG. 12b). Spacer 283 forms an additional lip part 283a which is situated between the ball 261 and the switch dome 281. Spacer 283 is formed by a non-conducting flexible material. Switch dome 281 provides a radially outwards force of sufficient magnitude that the ball 261 is forced radially outwards in the recessed annular channel 201a.

Upon moving the dosage selector 260 from the "parked position" (the EOD position) into its "ready position" (dose setting mode, 0 IU) shown in FIG. 12b, the ball 261 is forced radially inwards which moves the lip part 283a of spacer 283 inwards pressing the switch dome into its activated position which makes switching contact for the dome switch. The reverse movement will move the ball radially outwards breaking the switch circuit. As the EOD switch comprises an actuating element which moves at least partially in a radial direction upon entering EOD state, it is ensured that the switch timing is optimally synchronized with the actual movement of the dosage selector 260 into the EOD position. Hence, this configuration provides a superior solution with respect to tolerances as compared to solutions involving an axially moving switch. In addition, as the EOD switches are arranged in a balanced configuration, i.e. opposite each other which in this embodiment is 180 degrees, it is ensured that all EOD states are reliably detected, no matter if forces exerted on dosage selector contains a force component which forces the dosage selector in a direction away from one of the two EOD switches. The shown EOD switch configuration forms a superior switch and may find particular use in applications having small dimensions.

The two remaining ball lock mechanisms are somewhat simplified in that they only contain a leaf spring 262 (see FIG. 10) which forces the respective ball into the annular recessed channel 201a of the housing sleeve 201.

FIG. 14 depicts the guidance tube 250 onto which the Gray code sensor assembly 290 is affixed. As mentioned earlier, Gray code sensor assembly 290 is arranged for galvanically contact reading of Gray code cylinder 230 which encircles the Gray code sensor assembly 290. According to one aspect of the invention, by providing a reading assembly internally inside a circumferential arranged code, a large measuring diameter is readily obtainable which enables the forming of a detecting sensor of high precision.

Gray code sensor assembly 290 comprises a plurality of contact arms adapted to galvanically contact the Gray code cylinder 231, that is make galvanically contact to the conductive material sleeve 231a and to break contact when the contact arms are separated from the conductive material sleeve i.e. when the contact arms touch the electrically insulating areas of pattern 231b. Gray code sensor assembly 290 and Gray code cylinder 231 are adapted to provide both detection of the rotary movement of guidance tube and also to provide detection of whether the device is in dose setting mode or in dosage mode.

Three measuring contact arms 294a, 294b and 294c are arranged to wipe over the axially extending bars of the Gray code cylinder 230, as the guidance tube 250 rotates relatively to the toothed rim 230 during dose setting. Two other contact arms 292a and 292b are in continuous engagement with the conducting part of Gray code cylinder during all the various states that the device experiences during operation and defines a ground level. The two contact arms 292a and 292b forms a redundant connection to the electronic module 271. Furthermore, two additional contact arms 293a and 293b (in the following designated dosage sense "DS" switches) are disposed so as to be in contact with the electrically insulating circumferential continuous band of 231b when the device is in dose setting mode (additional reference is made to FIG. 7b). However, when the device is moved into dosage mode, due to the guidance tube 250 being shifted distally, the contact arms 293a and 293b are moved out of engagement with the electrically insulating circumferential continuous band and hence make galvanic contact with the Gray code cylinder 230. This invokes the detection of the mode change into dosage mode.

FIGS. 16 and 17 are schematic views serving to illustrate the proposed sensing scheme of the present invention. FIG. 16 shows the three contact arms 294a, 294b and 294c which can be moved relative to the track of conducting and non-conducting areas. Inside the Gray code cylinder 231 the pattern of conductive and non conductive areas (each being 15 deg. wide) are placed in intervals of 30°, hence comprising of 12 conductive and 12 non conductive areas arranged in a continuous loop. The active part is the Gray code sensor assembly comprising a set of 3 contact arms (SW1, SW2 and SW3) displaced 10° apart along the Gray code sequence track. It will be readily acknowledged that the contact arms of the Gray code sensor assembly may be arranged with other spacings while still obtaining the same sensor output as the Gray code sensor assembly rotates with respect to the Gray code cylinder. For example, in a situation where the contact arms SW1 and SW2 are arranged as shown on the figure, the contact arm SW3 may be moved a distance corresponding to one or more complete periods to either side. FIG. 17 is a schematic representation of the three contact arms 294a, 294b and 294c as they wipe over six consecutive distinct code positions (position 0 to 5). Each of the three contact arms will generate a code change when entering and leaving an isolated area. This configuration provides a total of 72 Gray code changes pr. revolution. In the depicted device which is a half-incremental injection device, the number of distinct rotational positions P pr. revolution is 36 and therefore each position that the dosage selector can be adjusted to correspond to two different adjacent Gray code states. Another embodiment may include a full-incremental injection device which may comprise 24 distinct rotational positions P pr. Revolution of dosage selector 260.

In accordance with the above, by selecting the present described Gray code sensor system which has 72 Gray code states, oversampling by a factor of either 2 or 3 can be chosen and hence the same sensor system can be used for both a half-incremental device as well as a full-incremental device. Since each mechanical position of the 36 position version corresponds to two adjacent Gray code states, ideally, it should be ensured that the transition between the two states is aligned to the mechanical dose adjustment, i.e. as determined by the click mechanism. In the 24 position version, each mechanical rest position corresponds to three adjacent Gray code states, and ideally, it should be ensured that the mechanical position as determined by the click mechanism falls in the middle of the central one of the three adjacent Gray code states. In the shown example, in a device having 24 distinct positions pr. revolution as compared with the 36 position version, the Gray code cylinder will have to be rotated slightly, e.g. by mounting the Gray code cylinder slightly rotated on toothed rim 230. The remaining modification when deriving the shown dose values on the display from the detected Gray code states may be carried out in software.

The Gray code of the shown embodiment is a 3-bit Gray code, with potentially 8 possible codes, of which only 6 possible codes are used. A logical high level is identified with "1" and a logical low level is identified with "0". The omitted codes are "000" and "111". If the Gray code sensor 290 senses a code of either "000" or "111", this will indicate a malfunction, and the injection device can be adapted to provide a warning. The 6 codes are repeated 12 times pr. revolution, hence this configuration additionally serves as a counter for counting revolutions of the dosage selector 260. This counter is necessary since setting a full dose on the described device involves more than one revolution.

The Gray code sensor will monitor the signals during setting of a dose and derive a best guess of the "set dose" from the collected information. In this pen mode the system is not accurate enough to determine the exact set dose but accurate enough to determine which part of the repeated code is active. Not until the moment where the set dose is finally decided, that is when the dose is fully delivered (EOD) and the clutch between guidance tube 250 and toothed rim 230 is engaged, is the system capable of determining the exact dose delivered. This is the pen mode where the tolerance situation is the most favourable and where an indirect detection of the clutch position between the guidance tube 250 and the toothed rim 230 is obtained. In alternative embodiments, the exact dose is determined at the point in time when the dosage selector changes to dosage mode, i.e. when the clutch teeth 250-2 of the guidance tube 250 gets into engagement with the set of teeth 230-2 of the toothed rim.

By counting the transitions from code position five to zero and combining this information with the semi-absolute readings before and after the dosage, the exact number of units can be determined. After the detection, the calculated dose is displayed on the display 275. An advantage of this semi-absolute setup is that the mechanical tolerances between dose setting mode and dosage mode can be eliminated.

The end of dose switches 280 tells the microcontroller that the dosage is completed. The switches must be triggered by a complete dosage or by winding down the dosage selector and depressing it after a partial dosage. A redundant switch is used for security reasons. Pull-up resistors for the switches are under software control to avoid using power when the switches are in the EOD state, the particular power saving method to be described in the following.

A second embodiment of a Gray code configuration will be described with reference to FIGS. 18, 19 and 22a-22d, wherein, instead of three gray code switches, the Gray code sensor assembly comprises four switch contact arms SW1, SW2, SW3 and SW4 which engages a modified Gray code sequence formed on an internal surface of the Gray code cylinder. As shown in FIG. 18, the Gray code cylinder comprises consecutive bands of electrically insulating areas (25 deg. wide) and electrically conducting areas (15 deg. wide) and thus having a period length of 40 deg., making room for 9 periods in one revolution. The four switch contact arms SW1, SW2, SW3 and SW4 are positioned 10 degrees apart along the Gray code track. Such configuration provides a Gray code sequence having 8 distinct codes in a Gray code sequence. The binary codes corresponding to this Gray code sequence can be viewed as well in FIG. 18 and also in FIG. 19. As will be discussed later, this Gray code sequence provides improvements having regard to power management as compared with the Gray code sequence of FIG. 17.

Referring now to FIG. 20a, a prior art contact switch arrangement is shown, such switch arrangement being typically included in medical delivery devices incorporating electronic circuitry where the switch is coupled to a control system. When using a control system to monitor the state or condition of a switch sensor, such as a contact switch sensor coupled to a movably arranged component for detecting its state or condition, switch sensors are normally connected to the control system by using a pull-up resistor, to ensure that the input has a well-defined high level when the switch sensor is open.

When the switch sensor is open, the input will be high and the current flowing in the resistor is zero. When the switch sensor is closed, the input will be low and the current flowing in the resistor can be calculated as the voltage divided by the resistance. This current will be present in all pull-up resistors where the corresponding switch sensor is closed. The current can be reduced either by reducing the voltage or by increasing the resistance. Reducing the voltage is normally not possible since it is defined by the rest of the logic circuitry, and increasing the resistance will make the system more sensitive to noise. Even though the current can be reduced by these methods, the sensor system will continuously consume power when the switch sensor is closed.

One way of solving this problem is to poll the input, meaning that he system micro-processor periodically will power up the sensor and check its state. The sensor power consumption will thus only be present very briefly, but the power consumption of the microprocessor must be taken into account as well. This means that the total power consumption depend on the polling interval and can be reduced by making the polling interval longer, but this will make the response time of the system slower. The choice of polling interval will thus be a trade-off between current consumption and response time.

The sensor described above will only consume power when the switch sensor is closed. This power consumption can be removed by putting the pull-up resistor under system control, as schematically depicted in FIG. 20b. When the switch is open, the output is set high, causing the input to become high, but with no power consumption. When the switch is closed, the input will become low and current will flow in the resistor. When the transition is detected by the microprocessor, the control output is turned off, and since the voltages on both sides of the resistor are now identical, no current will flow.

The sensor configuration shown in FIG. 20b is completely zero-power in both states. However, such solution is tied up with the problem that comes when the switch is opened again. Since the voltage at the top of the pull-up resistor is low, opening the switch will not cause the state of the input to change; the input will still be held in a well-defined low state by the pull-up resistor. This means that this system can detect a switch that closes, but not a switch that opens. Hence, such switch configuration may be used for only a limited number of applications.

In accordance with a further aspect of the present invention, a drug delivery device includes a switch configuration as schematically shown in FIG. 20c. In this configuration, in comparison with the switch configuration shown in FIG. 20b, a second switch is added, this switch having the opposite polarity of the existing switch. This way, there will always be one switch that is open. When the switch that is open closes, the pull-up for the other switch is turned on. When the other switch opens, the pull-up for the first switch is turned off. To ensure that the inputs are not left floating at any time, it is very important that the pull-up control output, whether high or low, is always active and not set to high-impedance state. In the switch configuration as shown in FIG. 20c, the switch sensor system will only consume power during the time it takes for the switch system to transfer from one stable state to another.

In the embodiments of drug delivery devices disclosed herein, the EOD switches and the dosage sense switches (DS) that senses whether the device is in dose setting mode or in dosing mode are configured to provide the complementary state shifting scheme as shown in FIG. 20c. However, as shown in FIG. 21, when the dosage selector is depressed during dosing both the EOD switches and the dosage sense switches (DS) are closed and current flows through their respective pull-up resistors. Normally, this should not lead to excessive power consumption since this situation only last as long as it takes to inject the selected dose. However, to further reduce energy consumption, a shift to an emergency polling scheme when this situation occurs may be implemented. An alternative solution would be to implement each of the switches as double, complementary switches. The power handling would then be local to each switch, but the mechanical side of this solution would be more complex.

Also the contact switches of the Gray code sensor are configured as switches connected to ground, and the inputs are held high by pull-up resistors. An open switch will not consume any power, but a closed switch will consume power because its corresponding pull-up resistor effectively will be connected between the supply voltage and ground. Hence, in accordance with the above described power saving scheme, the controller shuts down the pull-up switches for the switches that are closed and subsequently puts the controller into standby mode. This way, the sensor system will not consume power, but with this setup only changes that correspond to switches being closed can be detected. A switch that opens will not generate a rising voltage on its corresponding input since the pull-up resistor for that input has been shut down.

With the Gray code that is shown in FIG. 19, the transitions from positions 1 to 2, 3 to 4, 5 to 6 and 7 to 0 when going forward, and 1 to 0, 3 to 2, 5 to 4 and 7 to 6 when going backward can be detected and thus be used for powering up the shut-down pull-up resistors. This might be acceptable since the transitions counted when in dose setting mode are only indicative of the final result. A final corrective reading will be done when EOD mode is entered.

Ideally, the pull-ups should be implemented as external resistors connected to an I/O port on the processor. This will allow them to function as both pull-ups and pull-downs, thus keeping the inputs well-defined at all times.

EXAMPLE

The sensor is at Gray code position 1, so switch 3 is closed (0) and switches 1, 2 and 4 are open (1). The pull-up on switch 3 is turned off and 1, 2 and 4 are on. The processor goes into standby mode.

The sensor now changes to position 2. This means that switch 2 closes, so the input changes state to 0, waking up the processor. All pull-ups are then turned on and the inputs are read. Now the pull-ups on inputs 2 and 3 are turned off and the processor goes back into standby mode.

The sensor now changes to position 3. This means that switch 3 is turned off, but since the pull-up is disabled (or is pulled down) a transition of the input will not be detected. The processor will stay in standby mode and never detect the transition.

(end of example).

This scheme effectively implements a true zero-power sensor, but it lacks the ability to detect all the sensor transitions. A way of reducing this problem is to implement a more intelligent control of the pull-up resistors. Initially, only the pull-up resistors for open switches are activated. When a sensor transition is detected all pull-up resistors are activated, allowing the software to detect all sensor transitions, and a timer is started. Every time a sensor transition is detected, the timer is reset to its original value. When the timer times out, the system reverts to only having the pull-up resistors for open switches activated. This means that only the first transition in a series may be missed. The sensor will consume power during and shortly after state changes, but will be zero-power when static.

In FIG. 22a through 22d shows different states of the EOD switches and the DS Switch when the device is operated.

FIG. 22a shows the device in the storage condition where the device is in End-OF-Dose state. In this state, the dosage selector 260 is fully depressed and the EOD switches are active (open). An internal counter is reset to zero. The pull-up resistors for the EOD switches are on and the resistor for the dosage sense switch is off.

FIG. 22b shows the device where the user operates the device to prepare for dosing, i.e. by bulling out the dosage selector 260. This will change the state of the EOD switches and move the dosage sense switch away from the active position. In this state, the EOD switches are powered down, and the dosage sense sensor is powered up. Next the user will set the desired dose. This will generate pulses from the Gray code sensor system. These pulses, which include direction information, are used to update the internal counter with the number of Gray code transitions.

FIG. 22c shows the device where the user starts pressing the dosage selector 260 in order to inject the selected dose (exerted pressure is indicated by the triangular icon shown to the left). The contacts of the Gray code sensor system will move axially, but will not generate any pulses since the guidance tube 250 and the toothed rim 230 are locked together preventing rotation there between. The dosage sense switch will generate an event, causing the processor to power up the EOD switches so an event can be generated when EOD is reached. If the dosage selector is released before reaching EOD, the EOD switches are powered down again.

FIG. 22d shows the device in the EOD state where the EOD switches opens. The dosage sense sensor is powered down. A final Gray code reading is performed and the dosage amount can now be calculated based on the number of Gray code transitions. A button release and press will correctly give a result of zero units.

As noted above in referring to FIG. 3, the electronic circuitry includes a timer for measuring elapsed time since the latest performed injection. The timer is triggered by the EOD switches detecting when a current dose injection procedure is finalized. The relative time in hours are displayed but internally in the microprocessor provides better accuracy. Since no absolute time read-out is provided, the internal clock only operates with relative time and hence there is no need for procedures of setting the correct date and time of the device. Using the segments along the display periphery, a total of 12 hours can be represented, each hour being presented by 1 segment. When more than 12 hours have passed, all 12 segments are lit, and a full circle is shown.

FIG. 23a is an illustration of the operating procedure for invoking the displaying of the previously injected dose. After a time-out the display 275 is turned off to conserve power. However, to check the size of the latest injected dose or to check the time lapsed since that injection, the dosage selector 260 is pulled into the ready mode and pushed in into EOD state. Hereafter, the display 275 turns on for a prescribed duration.

FIG. 23b is an illustration of the operating procedure during a normal administration procedure. In the depicted embodiment, the display is turned off during dose setting and during dose injection so as not to cause any confusion relative to the reading of the mechanical dose indicator. At End-of-Dose, the display is turned on to display the size of the dose which has been injected.

With reference to FIG. 24 a second embodiment of a memory module for a drug delivery device will be described. Whereas the above-described first embodiment provides the user with information in respect of the last delivered dose (amount and time since delivery), the second embodiment is in addition to this feature provided with a memory for storing a number of data logs, each log comprising data representing a dose size and time stamp, as well as two-way wireless communication capability, this allowing the module to transmit and receive data to/from an external device. The recorded insulin injections are time stamped with the pens lifetime counter, in seconds. A CRC checksum is calculated and the whole record (dose, timestamp and checksum) is stored and arranged cyclic, i.e. when the memory is full, the newest record will overwrite the oldest) in a non volatile memory (EEPROM) which is only powered when read from or written to. The memory may be designed to hold data from e.g. 3 months of average use of the drug delivery device. In an exemplary embodiment the drug delivery device is designed to upload its data log to an external database, e.g. PC, PDA, docking station, cell phone or data network.

The construction of the second embodiment is essentially identical to the construction of the first embodiment. More specifically, it comprises an electronic module in the form of a folded PCB attached to a display 1280 and arranged in an electronic module housing which again is arranged in the dosage selector housing 1260, the display being covered by a display window 1270.

The means for detection of movement between the different components of the drug delivery device during dose setting and dose expelling are the same. Also the contacts 280 for detecting whether the dosage selector housing is in its parked position (EOD state) or in an actuated pulled-out position are the same.

The PCB is provided with an extension "finger" 1290 which in its folded position is arranged in the gap between the display and the dosage selector housing, the extension and PCB in general being provided with additional and upgraded memory and processor components as well as additional components adding two-way wireless communication capability to the memory module. The shown embodiment is provided with an IR transmitter 1291 and a corresponding IR photo transistor receiver 1292, however, wireless communication could be based on other suitable means e.g. RF or induction.

The display and the IR transmitter/receiver are arranged under a common display cover 1270 inserted in the proximal end opening of the dosage selector housing. Compared to the above-described embodiment the display window has been modified to serve as lenses and filters for the IR transmission means. More specifically, the display window comprises a main transparent portion 1271 into which a smaller IR cover 1275 is inserted, e.g. by composite injection moulding. The IR cover is made from a coloured (here: red) plastic serving as a filter for the IR transmission and receiving means. The IR cover is further provided with two protruding lenses 1276 serving to focus the IR light generated by the IR transmitter into a beam and to focus the IR light received from an external IR source onto the IR receiving photo transistor. Alternatively a combined transmitter/receiver using a single lens could be used. In addition to serve as lenses, the protrusions also indicate to the user where the transmitter/receiver is located, this providing an aid to avoid blocking transmission, e.g. by a finger.

Irrespective of the memory module of the invention is provided to users as a sealed unit in which the power source cannot be exchanged, or it is provided with an exchangeable power source, it is desirable to ensure long operational life of the power source. This is indeed the case for all electronic devices, however, for a memory module relying on relatively small build-in electric cells and provided with relatively power hungry wireless transmission means (e.g. IR), it is desirable to keep especially the time in which the transmission means are in operation to a minimum. This said, use and operation of a drug delivery device provided with wireless transmission means should be as easy as possible without requiring the user to perform special operations to turn on and off the different functions of the device.

Correspondingly, in a further aspect of the present invention a drug delivery device is provided comprising first user-operatable means for setting a dose of drug to be expelled, second user-operatable means for expelling a set dose from a drug reservoir, and electronic circuitry for storing and communicating data. The electronic circuitry has a low-power hibernating state, and a (first) operating state, just as contacts (e.g. galvanic or inductive contacts) for energizing the electronic circuitry from the hibernating to the operating state is provided. To allow ease of use simple user manipulation of the first or second user-operatable means actuates the contacts to thereby energize the electronic circuitry from the hibernating to the (first) operating state. In the shown embodiments a combined user-operatable dosage selector and expelling member (in the following just "dosage selector") is provided, the member being rotationally as well as axially displaceable to provide the first respectively the second user-operatable means. Depending on the actual design of the dose setting and expelling mechanism of the drug delivery device, the dosage selector may or may not rotate as it is moved axially to expel a set dose. In case the dosage selector is designed to rotate it may be provided with an upper, proximal surface which is allowed to rotate relative to the main body of the dosage selector, this preventing sliding action between the dosage selector and the user's finger pushing down the dosage selector to expel a dose. As described above, in the shown embodiments the dosage selector has a pushed-down "parked" position in which it cannot be rotated but from which it can be pulled out to a "ready" position in which the electronic circuitry is energized.

Correspondingly, when the memory module is provided with communication means for wirelessly transmitting and/or receiving data, the communication means has a sleep state in the hibernating state and an energized state in the (first) operating state. As appears, when the user decides to "turn on" the delivery device by moving the combined member out of its parked position, both the communication means for wirelessly transmitting and/or receiving data and the detection means for detecting and storing data representing an amount/time log for the drug expelled from the drug delivery device is energized, however, unless the user wants to use the communication capability it should be turned off as soon as possible to safe energy, however, this should ideally happen without the user is involved.

Thus, the electronic circuitry may have a second operating state, wherein the first operating state has a first level of power consumption and the second operating state has a second lower level of power consumption, wherein the operating state changes from the first to the second level when a first pre-set condition is met, and wherein the operating state changes from the second level to the hibernating state when a second pre-set condition is met.

Turning to the second embodiment of the present invention the electronic circuitry comprises communication means for wirelessly transmitting and/or receiving data, the communication means having a sleep state in the hibernating state, an energized state in the first operating state, and a sleep state in the second operating state, and detection means for detecting and storing data representing an amount/time log for drug expelled from the drug delivery device, the detection means having a sleep state in the hibernating state, and an energized state in the first and second operating states.

In other words, the second embodiment of the present invention has a low-power hibernating state in which both of the main functions (i.e. the detection and the communication means) are in a low-power sleep modus, a high-power state in which both the detection and the communication means are in an energized high-power state, and a medium-power state in which the detection means are in an energized high-power state and the communication means are in a low-power sleep modus.

For the exemplary second embodiment the intended way of use of the communication feature is as follows. The user first turns on the communication interface of the device to which data is to be transferred, e.g. a PC equipped with an Accu-Chek® Smart Pix communication interface from Roche Diagnostics. The Accu-Chek Smart Pix Device Reader is a small device which wirelessly imports and displays data from e.g. Accu-Chek blood glucose meters, Accu-Chek software for handhelds and Accu-Chek insulin pumps, via a built-in infrared interface. The Accu-Chek Smart Pix Device Reader is provided to help individuals with diabetes and healthcare professionals to view and analyse blood glucose/insulin data quickly and conveniently.

A proprietary communication protocol (software) was developed to handle the communication sequence between the memory module and an adapted version of the Smart Pix Reader. The protocol was optimized to use as little power as possible when run by the memory module. The protocol uses a command/response model where the drug delivery device (e.g. pen system), when activated waits ("listen") for a command and responds accordingly. Commands are implemented for requesting the full log or parts of the log. In order to save power the protocol can analyse the data content and inverse the bits so that as few IR light pulses as possible will be transmitted from the pen. To further save energy the receiver could be adapted to measure the strength of the received signal and correspondingly adapt the strength of the transmitted signal. Indeed, the protocol could also be used to handle e.g. RF communication. As described above, the memory module logs a given dose together with a time value in seconds, the timer being a "lifetime counter" starting to count from zero when the memory module is turned on for the first time. When the logs are transferred to the receiving device the protocol will translate the time stamp values into traditional real-time time stamps based on the receiving device' internal clock.

When the Smart Pix device is first attached to a PC using its USB interface, it will start to transmit a code identifying the transmitter as a Smart Pix device. Secondly, the user turns on the memory module by moving the dosage selector from its parked to its ready position, this starting the IR receiver which for a predetermined amount of time (e.g. 20 seconds) will listen (or "look") for a Smart Pix (or any other recognizable) signal. If a recognizable signal is detected the two devices will "shake hands" and if the pre-defined conditions for transmission of data are verified (e.g. the specific memory module has previously been paired with a given PC, e.g. using the serial number of the memory module) the memory module will start to transmit data, e.g. all log data stored in the memory module or only data specified by the receiving device. The memory module may continue to transmit data until an acknowledgement signal is received from the receiving device or after having transmitted data for a predefined amount of time. Whether the memory module is adapted to either first listen and then transmit or the opposite should be determined by the component using the least energy, e.g. the receiver for IR communication.

In case the user does not want to transmit data, the user will simply start to set a dose by rotating the dosage selector away from its ready position, this immediately bringing the communication means into sleep mode. The user may also cancel all operations by simply moving the dosage selector back into its parked position after which the communication means is also brought into sleep mode.

Compared to today's use of manual logbooks, an electronic logbook will be more reliable, data vice, and more updated. This will help health care professionals to better monitor patients and to make better judgments based on the information provided. Furthermore the patient will be relived of the work with filling out the manual logbook, all leading to better compliance.

Some preferred embodiments have been shown in the foregoing, but it should be stressed that the invention is not limited to these, but may be embodied in other ways within the subject matter defined in the following claims. For example, the gear mechanism may be substituted by other gear mechanisms including the ones shown in WO 2004/078239, EP 1610848 and WO 99/38554.

The invention claimed is:

1. A drug delivery device for setting and injecting set doses of a drug from a drug-filled reservoir comprising a Gray code type detector for detecting relative movement between a first element and a second element during dose setting and/or during injection, said Gray code type detector comprising:
   a plurality of alternating first and second areas disposed on said first element, wherein said first and second areas are configured to first and second states, respectively, and wherein each of said first areas comprise width $X_1$ and each of said second areas comprise width $X_2$, and
   wherein a plurality of detectors comprises m detectors, wherein m is at least three wherein each of the m detectors is disposed on said second element and is configured to sense said first and second states
   wherein said detectors are arranged in a direction respective to said first and second areas' longitude so as to sense said first and second states and provide a reading sequence of a Gray code scheme when said detectors are moved relatively to said first and second areas.

2. A drug delivery device as in claim 1, wherein said plurality of alternating first and second areas disposed on said first element is arranged as a circumferential band on a cylindrical surface, either on an interior cylindrical surface or an external cylindrical surface.

3. A drug delivery device as in claim 1, wherein said first element includes at least one additional area adapted to be sensed by one or more additional detector(s), said additional detector(s) being arranged on the second element for sensing movements relative to said plurality of alternating first and second areas in directions transverse to the direction along said Gray code scheme.

4. A drug delivery device as in claim 3, wherein said drug delivery device includes a dose setting member and an injection button, wherein rotational movements of said dose setting member is detected by said Gray code type detector, and wherein said additional detector(s) are configured to detect whether or not an injection force is applied to said injection button.

5. A drug delivery device as in claim 1, wherein said plurality of alternating first and second areas includes areas of electrical conducting and electrical non-conducting materials, respectively, and wherein said at least three detectors are contact switches arranged to electronically sense the presence or absence of an electrical conducting material.

6. A drug delivery device as in claim 1, wherein said at least three detectors forms a reading assembly for detecting relative rotational position changes between said first element and said second element during dose setting and/or during dose injection, and wherein said plurality of alternating first and second areas to encircle said reading assembly.

7. A drug delivery device as in claim 1, wherein said plurality of alternating first and second areas is arranged as a helically extending track.

8. A drug delivery device as in claim 1, wherein said plurality of alternating first and second areas and said at least three detectors forms a single Gray code scheme or a multitude of repeated Gray code schemes forming a total scheme code length n.

9. A drug delivery device as in claim 8, wherein said detectors are contact switches.

10. A drug delivery device as in claim 9, wherein at least one of said contact switches is closed upon at least every other state change in either direction from a present position, said present position being selected from any of each possible n position.

11. A drug delivery device as in claim 8, wherein said drug delivery device includes a rotatable dosage selector associated with said second element and being rotatable in a number of distinct rotational positions P spanning a single revolution, wherein said Gray code type detector is configured for detecting rotational position of said dosage selector and wherein said total scheme length n is selected as two, three or four times P.

12. A drug delivery device as in claim 1, wherein said at least three detectors comprise three, four, five, six or seven detectors.

* * * * *